(12) United States Patent
Font Perez et al.

(10) Patent No.: US 10,226,480 B2
(45) Date of Patent: Mar. 12, 2019

(54) BIOMATERIAL FROM WHARTON'S JELLY UMBILICAL CORD

(75) Inventors: Julio Font Perez, Bilbao (ES); Maria Begoña Castro Feo, Leioa (ES); Maite Del Olmo Basterrechea, Sopelana (ES)

(73) Assignee: HISTOCELL, S.L., Derio, (Bizkaia) (ES)

( * ) Notice: Subject to any disclaimer, the term of this patent is extended or adjusted under 35 U.S.C. 154(b) by 418 days.

(21) Appl. No.: 13/638,535

(22) PCT Filed: Mar. 30, 2010

(86) PCT No.: PCT/EP2010/002011
§ 371 (c)(1),
(2), (4) Date: Dec. 17, 2012

(87) PCT Pub. No.: WO2011/120535
PCT Pub. Date: Oct. 6, 2011

(65) Prior Publication Data
US 2013/0095143 A1    Apr. 18, 2013

(51) Int. Cl.
| | | |
|---|---|---|
| *A61K 31/726* | (2006.01) | |
| *A61K 8/04* | (2006.01) | |
| *A61K 8/98* | (2006.01) | |
| *A61L 27/26* | (2006.01) | |
| *A61L 27/56* | (2006.01) | |
| *A61L 27/52* | (2006.01) | |
| *A61K 35/30* | (2015.01) | |
| *A61K 35/14* | (2015.01) | |
| *A61K 35/12* | (2015.01) | |
| *A61K 31/727* | (2006.01) | |
| *A61Q 19/08* | (2006.01) | |
| *A61K 8/73* | (2006.01) | |
| *A61K 35/44* | (2015.01) | |
| *A61K 35/36* | (2015.01) | |
| *A61K 35/35* | (2015.01) | |
| *A61K 35/34* | (2015.01) | |
| *A61K 35/33* | (2015.01) | |
| *A61K 35/32* | (2015.01) | |
| *A61K 9/00* | (2006.01) | |
| *A61K 9/06* | (2006.01) | |
| *A61K 31/737* | (2006.01) | |
| *A61K 47/36* | (2006.01) | |
| *A61K 31/728* | (2006.01) | |
| *A61K 45/06* | (2006.01) | |

(52) U.S. Cl.
CPC ............ *A61K 31/726* (2013.01); *A61K 8/042* (2013.01); *A61K 8/73* (2013.01); *A61K 8/735* (2013.01); *A61K 8/982* (2013.01); *A61K 9/0024* (2013.01); *A61K 9/06* (2013.01); *A61K 31/727* (2013.01); *A61K 31/728* (2013.01); *A61K 31/737* (2013.01); *A61K 35/12* (2013.01); *A61K 35/14* (2013.01); *A61K 35/30* (2013.01); *A61K 35/32* (2013.01); *A61K 35/33* (2013.01); *A61K 35/34* (2013.01); *A61K 35/35* (2013.01); *A61K 35/36* (2013.01); *A61K 35/44* (2013.01); *A61K 45/06* (2013.01); *A61K 47/36* (2013.01); *A61L 27/26* (2013.01); *A61L 27/52* (2013.01); *A61L 27/56* (2013.01); *A61Q 19/08* (2013.01); *A61K 2800/91* (2013.01); *A61L 2400/06* (2013.01); *A61L 2430/06* (2013.01); *A61L 2430/34* (2013.01)

(58) Field of Classification Search
None
See application file for complete search history.

(56) References Cited

U.S. PATENT DOCUMENTS

| | | | | |
|---|---|---|---|---|
| 6,017,546 | A * | 1/2000 | Glover | 424/401 |
| 2005/0013870 | A1* | 1/2005 | Freyman et al. | 424/520 |
| 2005/0131790 | A1* | 6/2005 | Benzschawel | G06N 3/02 705/35 |
| 2006/0089721 | A1* | 4/2006 | Muhanna et al. | 623/17.16 |
| 2006/0199263 | A1* | 9/2006 | Auger et al. | 435/366 |
| 2009/0155362 | A1* | 6/2009 | Longin | C08B 37/0072 424/484 |
| 2012/0315259 | A1* | 12/2012 | Friedlander | 424/93.71 |

OTHER PUBLICATIONS

Gogiel et al. The International Journal of Biochemistry and Cell Biology.*
Segura et al. Biomaterials 2005 26:359-371.*
Sobolewski et al. Biology of the Neonate 1997 71:11-21.*
Vogel et al. Isolation of Proteoglycans for Tendon in Methods in Molecular Biology: Proteoglycan protocols Walker et al. ed. Humana Press: Totowa 2001:171:9-17.*
Romnowicz et al. Folia Histochemica et Cytobiologica 1994:32(3) 199-204.*
Bryan Effects of extracellular matrices on porcine umbilical cord matrix stem cells 2008.*
The International Journal of Biochemistry and Cell Biology 2003 35:1461-1469 (Year: 2003).*
Mensitieri et al. Journal of Materials Science: Materials in Medicine 1996 7:695-698 (Year: 1996).*
Gomez-Alejandre et al. International Journal of Biological Macromolecules 2000 27:287-290 (Year: 2000).*

* cited by examiner

*Primary Examiner* — Robert A Wax
*Assistant Examiner* — Caralynne E Helm
(74) *Attorney, Agent, or Firm* — Sughrue Mion, PLLC

(57) ABSTRACT

The present invention relates to a biomaterial, specifically a hydrogel, based on the extracellular matrix of the umbilical cord for its application in regenerative medicine. The invention particularly relates to a biomaterial made up of glycosaminoglycans present exclusively in the Wharton's jelly of the umbilical cord (which can optionally be combined with cells as a combination therapy), and also to the methods for the production and use thereof.

19 Claims, 12 Drawing Sheets

FIG. 10
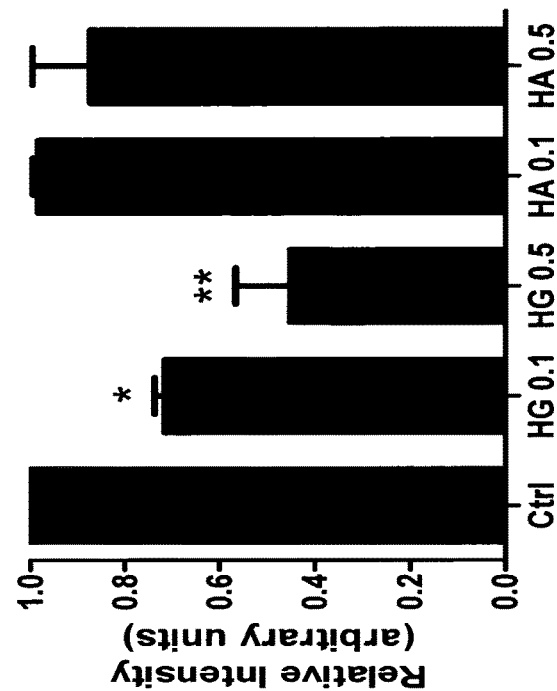
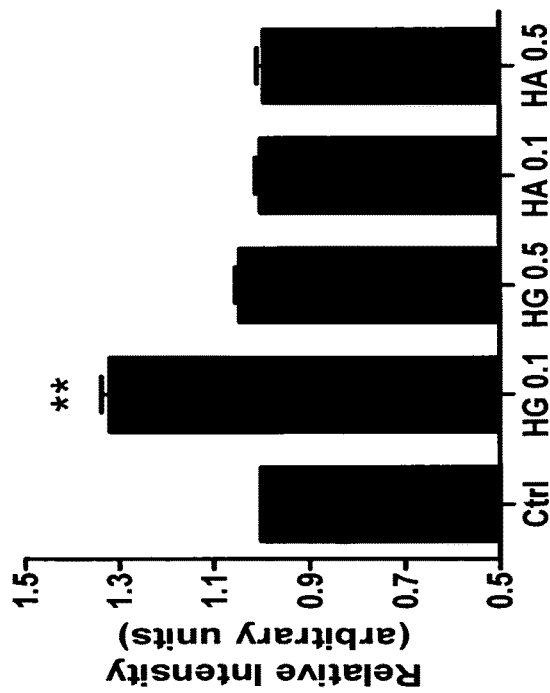

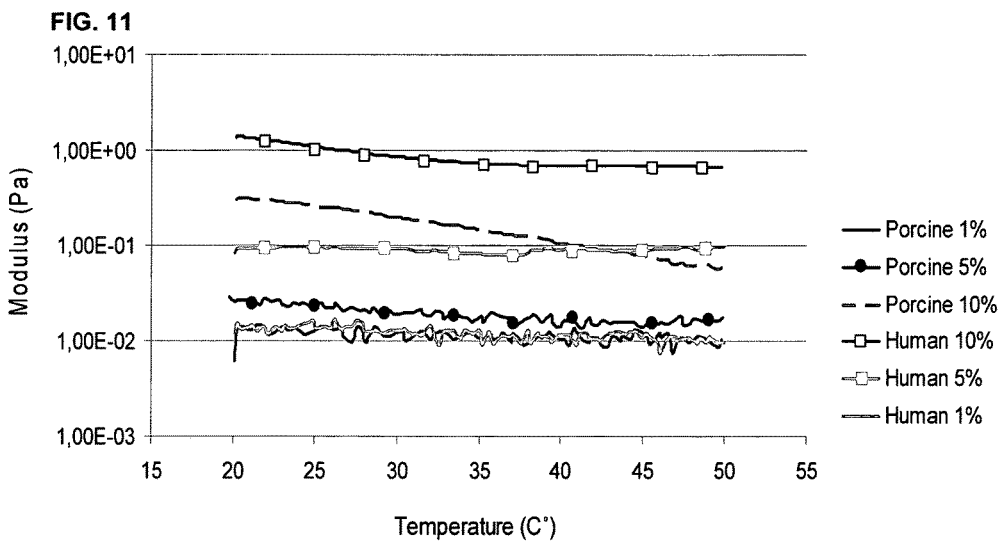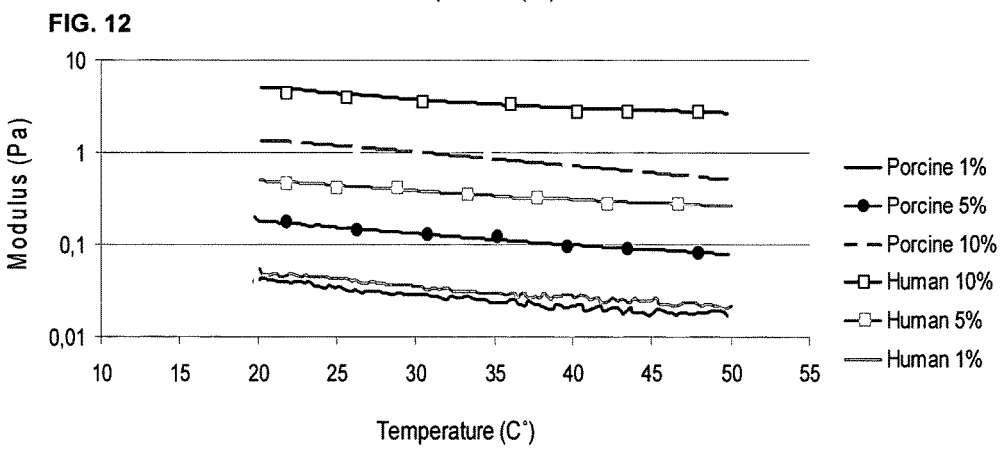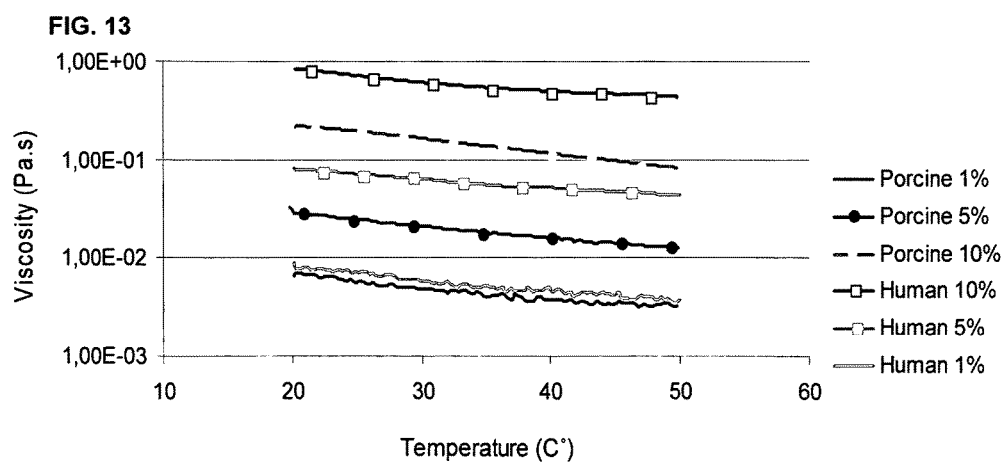

BIOMATERIAL FROM WHARTON'S JELLY UMBILICAL CORD

CROSS REFERENCE TO RELATED APPLICATIONS

This application is a National Stage of International Application No. PCT/EP2010/002011, filed on Mar. 30, 2010, the contents of all of which are incorporated herein by reference in their entirety.

TECHNICAL FIELD OF THE INVENTION

The present invention relates to a biomaterial, specifically a hydrogel, formed from the extracellular matrix of the umbilical cord for its application in regenerative medicine. The invention particularly relates to a biomaterial made up essentially of the glycosaminoglycans present exclusively in the Wharton's jelly (WJ) of the umbilical cord, and also to the methods for the production and use thereof. Embodiments of the product can be used solely, or in combination with cell-based therapies.

BACKGROUND OF THE INVENTION

The biomaterials formed by polymers play a central role in regenerative medicine since they provide temporary three-dimensional anchors for the adhesion, proliferation and the differentiation of transplanted cells. This three-dimensional structure provides a suitable platform for intercellular communication and the relationship of the cells with the components of the biomaterial. The biointeraction occurring between the matrix and the cells over time determines the proliferative capacity of the cells, their organization for the formation of a new tissue, their differentiation and the secretion of signaling molecules which direct the regenerative process (Dawson et al., 2008).

In order for these phenomena to occur, it is necessary for the biomaterial to remain in the site of application for a limited time until its reabsorption, conserving its structure long enough for a suitable cellular action with regenerative consequences.

Hydrogels, a specific type of biomaterial, have a number of properties that make them suitable for their application in tissue engineering.

Hydrogels are structures formed by interconnected hydrophilic polymers of a natural or synthetic nature, with the capacity to contain a large amount of water inside their structure, from 10-20% up to hundreds of times their own weight. These gels show a semi-solid morphology with a three-dimensional lattice that is an ideal candidate for forming a structural matrix capable of acting as a support. This three-dimensional structure can be formed by both physical crosslinking and by chemical crosslinking. Physical crosslinking leads to reversible hydrogels the structure of which can be reversed according to the end application, whereas covalent chemical crosslinking leads to permanent hydrogels, the structure of which will be maintained through the entire application (Coburn et al., 2007). Therefore, hydrogels are polymer materials (of a natural or synthetic nature) crosslinked in the form of a three-dimensional network which swell in contact with water, forming soft elastic materials, and which retain a significant fraction thereof in their structure without dissolving.

Hydrogels have a series of particular characteristics, such as:

1. Hydrophilic nature: due to the presence in their structure of water-soluble groups (—OH, —COOH, —CONH$_2$, —CONH, SO$_3$H). They have a high water content similar to that of native tissues (Elisseeff at al., 2005).
2. Insoluble in water: due to the existence of a cohesive three-dimensional polymer network in their structure.
3. They have a gelatinous consistency which is determined by the hydrophilic starting monomer and the low crosslinking density of the polymer.

They have the capacity to swell in the presence of water or aqueous solutions, considerably increasing their volume until reaching chemical-physical equilibrium, but without losing their form. This capacity to swell provides an aqueous microenvironment comparable to that which the cells are subjected to in soft tissues. The presence of water and of a porous structure also allows the flow of low molecular weight solutes and of nutrients that are crucial and essential for cell viability, as well as the transport of cell wastes outside of the hydrogel (Torres et al., 2000).

Glycosaminoglycans (GAGs), also referred to as mucopolysaccharides, are heteropolysaccharides found in organisms bound to a protein nucleus forming macromolecules referred to as proteoglycans. These can be found on the surfaces of cells or in the extracellular matrix and carry out important functions for cell-cell and cell-extracellular matrix interactions. They are in sulfated and non-sulfated forms with a common characteristic molecular moiety involving a repeated sequence of disaccharides formed by two different sugars: one of them is usually a hexuronate while the other one is a hexosamine. The configurational variation in the bonding of the disaccharides and the position of sulfation leads to an increase of the diversity in the physical and chemical properties of these chains. The high sulfate content and the presence of uronic acid confers to GAGs a large negative charge, so the large amount of GAGs in WJ make this tissue be extremely hydrophilic.

There are several types of GAGs, which are directly involved in basic cell functions, not only due to their structure, but also because they are anchor sites for several cell signaling molecules.

Hyaluronic acid is the most abundant GAG in WJ. It is the only non-sulfated member of the GAG family which functions in vivo like a free carbohydrate, its structure consisting of repeats of a disaccharide: D-glucuronic acid and (1-β-3) N-acetyl-D-glucosamine (Goa et al., 1994; Laurent et al., 1992). It is synthesized by several cell types and is secreted into the extracellular space where it interacts with other components of the extracellular matrix to create the support and protection structure surrounding the cells (Collins et al., 2008). It is a large, polyanionic linear polymer possessing single molecules that can have a molecular weight of 100,000 to 5×10$^6$ Da (Toole et al., 2004; Bertolami et al., 1992). It has a coiled structure taking up a large volume, leading to high viscosity solutions. The individual molecules of hyaluronic acid associate with one another, forming networks or lattices. In developing tissues, hyaluronic acid is considered the main structural macromolecule involved in cell proliferation and migration.

Hyaluronic acid has been involved in several processes, such as vascularization, morphogenesis, and in the general integrity and repair of the extracellular matrix. It is known that a large amount of hyaluronic acid contained in amniotic fluid favors the repair of fetal wounds (Longaker at al., 1989). Variations in its molecular properties between healthy skin and scars have furthermore been observed, hyaluronic acid of typical scarring being different from that of hypertrophic scarring (Ueno at al., 1992).

Chondroitin sulfate is a linear polymer formed by a D-glucuronic acid dimer and N-acetylgalactosamine repeat. Its usefulness has been tested in therapies targeted against joint diseases by means of inhibiting the activity of the enzymes responsible for the degradation of the matrix of the cartilage components. It can act as an anti-inflammatory by means of the inhibition of the complement and is useful in the treatment of thromboembolic disorders, in surgery and ophthalmological clinics.

Dermatan sulfate, also known as' chondroitin sulfate B, is a potent anti-coagulant due to its selective inhibitory effect on thrombin through heparin cofactor II, being very effective in vivo due to its lower hemorrhagic risk (Trowbridge at al., 2002).

Glycosaminoglycans in general and heparin in particular, have the capacity to modulate plasma cascade activity, enhancing the inhibition of the intrinsic coagulation pathway and inhibiting the classic complement activation pathway at different points (Rabenstein, 2001). Other known functions of the heparin are the inhibition of angiogenesis, humoral growth and its antiviral activity.

Heparan sulfate has a structure that is closely related to heparin. It is widely distributed in animal tissues and among its functions, cell adhesion and the regulation of cell proliferation, are paramount. It has a protective effect against the degradation of proteins, regulating their transport through the basement membrane and also intervening in the internalization thereof (Rabenstein, 2001).

There are several patent documents relating to mucopolysaccharides obtained from human or animal origin. Document U.S. Pat. No. 3,887,703 relates to mixtures of mucopolysaccharides obtained from the cutaneous teguments and umbilical cords from a fetal bovine or fetal ovine source. The process to obtain the mucopolysaccharides in the aforementioned patent does not describe the removal of membrane, cells, and vascular components of the umbilical cords. The extraction product is obtained in the form of a powder without a clear compositional or quantitational understanding of the individual mucopolysaccharides contained therein. The active products are identified by the amount of hexosamines that are present in the mixture. Compositions in both injectable and oral ingestion forms for the treatment of oily scalp and hair, and for inflammations, are prepared with the extracts.

U.S. Pat. No. 5,814,621 relates to a composition essentially consisting of a drug which is more soluble in an organic solvent-water mixture than in water, and a mucopolysaccharide forming part of a drug, in which crystals or particles of the drug are distributed on the surface of the particles of the mucopolysaccharide and in which said drug dissolves in water more quickly than if it were alone. Said composition can be in the form of granules.

Patent application WO 2008/021391 A1 describes biomaterials comprising the umbilical cord membrane. Furthermore, it can additionally comprise one or more umbilical cord vessels and/or Wharton's jelly. The biomaterial is preferably dry and can be flat, tubular or shaped to fit a particular structure. The invention also provides methods of making the biomaterial comprising at least one layer of the umbilical cord membrane, as well as the methods for obtaining said biomaterials and the use thereof for repairing tissues or organs.

The description characterizes the biomaterial from the umbilical cord. It describes that the composition of said material comprises collagen (type I, III and IV, these being 75-80% of the percentage of the matrix of the biomaterial), fibronectin and glycosaminoglycans.

It is also mentioned that the biomaterial can also comprise collagen that does not come from umbilical cords and has a commercial origin, or it has been isolated from other tissues and methods known in the state of the art. The authors also add that the biomaterial can comprise non-structural compounds such as growth factors, hormones, antibiotics, immunomodulatory factors, etc.

Spanish patent ES 8600613 describes a process for the treatment of body tissues, for separating cell membranes, nucleic acids, lipids and cytoplasmic components and forming an extracellular matrix the main component of which is collagen, and for making the body tissue suitable for being used as a body graft, comprising extracting said tissue with at least one detergent while at the same time it is maintained with a size and shape suitable for the grafting thereof in the body.

Patent document ES2180653T3 describes methods for transforming biological materials into substances which have experienced autolysis for eliminating at least 70% of the cells and methods for the treatment of said material for inhibiting its mineralization after implantation in a human or animal. It claims that the starting biological material can be, among others, the umbilical cord; although it specifically relates to an aortic valve of a pig. Nevertheless, the description does not contain any detail with respect to carrying it out with umbilical cord. The resulting biomaterial is used to create a bioprosthetic heart valve.

Patent document U.S. Pat. No. 4,240,794 relates to preparing human or other animal umbilical cords for their use as a vascular replacement. The document specifically describes a technique for dehydrating the umbilical cord in alcohol followed by a method for fixing it in the desired configuration. It is described that once the umbilical cord has been cleaned of possible remains of other tissues, it is mounted on a mandrel and immersed in a specific ethyl alcohol solution for the time necessary for it to dehydrate. After dehydration, the cord is immersed in a 1% aldehyde solution for fixing.

Patent document FR 2,563,727 describes a method for producing a skin graft from deprogrammed connective tissue impregnated with Wharton's jelly and stored at freezing temperatures. The authors describe a device which is anchored to the umbilical tissue and it is expanded by means of a cannula which injects compressed air. It is described that the umbilical cord is then cut and isolated but the product resulting from this process is not made up of WJ exclusively.

There are patent documents which use umbilical cord to obtain cells of interest, for which purpose they carry out processes for separating Wharton's jelly and eliminating it, thus obtaining said cells. For example, PCT document 98/17791 describes the isolation of pre-chondrocytes from the umbilical cord, which are subsequently used therapeutically to produce cartilage. Similarly, in document WO 2004/072273 A1 progenitor cells are extracted from Wharton's jelly that lies within the perivascular region of the umbilical cord and are used to repair human tissues.

Unlike other similar biomaterials, the biomaterial of the present invention is made up of a combination of different GAGs present in the WJ of the umbilical cord. It is mostly made up of hyaluronic acid, but furthermore, unlike other GAG compounds, it contains dermatan sulfate, heparan sulfate, heparin, keratan sulfate, chondroitin-4-sulfate and chondroitin-6-sulfate. The specific combination of the different GAGs as present in the WJ of the umbilical cord improves the bioactivity of the biomaterial, since each of them carries out cell behavior regulatory functions. For example, it is known that heparan sulfate and heparin are the main binding sites for FGF and EGF (Kanematsu et al., 2003; Ishihara et al., 2002), which protect them from proteolysis and allow local concentrations of these factors in the cell environment, creating the molecular microenvironment suitable for large cell activation (Malkowski et al., 2007)

However, to the best of our knowledge, there is no document that mentions a biomaterial formed by GAGs derived from Wharton's jelly of umbilical cord that is: 1) free of umbilical cord membrane and blood vessels, 2) which can form a hydrogel with tunable viscosity, 3) which is applicable to a wide range of human pathologies. Moreover, the aforementioned patent examples contain umbilical-derived products that differ significantly from the current embodiment presented in this document. The biomaterial of the present invention is based on the glycosaminoglycans exclusively forming the extracellular matrix of the umbilical cord referred to as WJ. Thus, although numerous attempts to synthesize extracellular matrix are found in the literature, an exact composition that simulates the natural conditions of a specific tissue has not been achieved.

The biomaterial developed in the present invention may offer a three-dimensional scaffold which has potential applications as a base matrix for tissue engineering. Furthermore, when applied directly or combined with cells as a construct in a pathology, it intervenes in the regenerative process, exerting a chemotactic effect on the cells of the surrounding tissue thus providing a favorable environment for the activation of cell processes.

The combination of GAGs present in this biomaterial provides a number of specific signaling molecule binding sites which will allow in the application site high activation of the cells of the tissue itself for the synthesis of high levels of extracellular matrix which will regenerate and repair the treated defect.

Furthermore, the origin of the biomaterial of the invention provides a natural product of human or animal origin from a non-immunogenic area. This material is eliminated through natural biodegradation processes in the body, thus preventing the undesirable reactions or side effects caused by other biomaterials. For example, some synthetic biomaterials may cause inflammation, induration (hardening of organ tissues), onset of granulomas, necrosis in mucosae, and tissue complications due to the toxicity of the substances used in the production thereof.

One of the most important functions of the GAGs in the umbilical cord is to provide strength, elasticity and resistance for protecting the vascular system located therein from external physical disturbances (e.g. kinking of the cord would be fatal to the fetus). In fact, the deficiency in the synthesis of these molecules is involved in important pathologies during pregnancy (Gogiel et al., 2005). Therefore, it is believed that a biomaterial made up of the 7 different types of GAGs forming part of the umbilical cord would possess a large degree of versatility through possession of the following capabilities: recapitualtion of the bioactivity that occurs in the organism, possession of the same mechanical properties that benefit the umbilical cord, and possession of the suitability for further processing and modification (such as crosslinking).

DESCRIPTION OF THE DRAWINGS

FIG. 10: RT-PCR of the expression of Collagen II and Versican. Results from the densitometric scanning of the agarose gels. Data are expressed as arbitrary units of intensity relative to the control value (C) and are the mean±s.e.m, n=3. (*p<0.05, **p<0.01). The image shows the onset of type II collagen expression and the waning of the Versican in the AMSCs arranged on the biomaterial of the present invention. These expression characterisitics are indicative of the cells in the process of differentiation towards a chondrocyte phenotype and synthesis of extracellular matrix corresponding to mature articular cartilage.

FIG. 11: Storage modulus results for three different concentrations of the biomaterial of the present invention derived from porcine and human sources. Data was collected from a single excitation frequency/strain derived from the respective linear viscoelastic regions of the samples. A temperature sweep over temperatures bracketing physiological values yielded a viscoelastic temperature relationship for all samples.

FIG. 12: Loss modulus results for three different concentrations of histogel derived from porcine and human sources. Data was collected from a single excitation frequency/strain derived from the respective linear viscoelastic regions of the samples. A temperature sweep over temperatures bracketing physiological values yielded a viscoelastic temperature relationship for all samples.

FIG. 13: Loss modulus results for three different concentrations of the biomaterial of the present invention derived from porcine and human sources. Data was collected from a single excitation frequency/strain derived from the respective linear viscoelastic regions of the samples. A temperature sweep over temperatures bracketing physiological values yielded a viscoelastic temperature relationship for all samples.

DETAILED DESCRIPTION OF THE INVENTION

Figure 1:
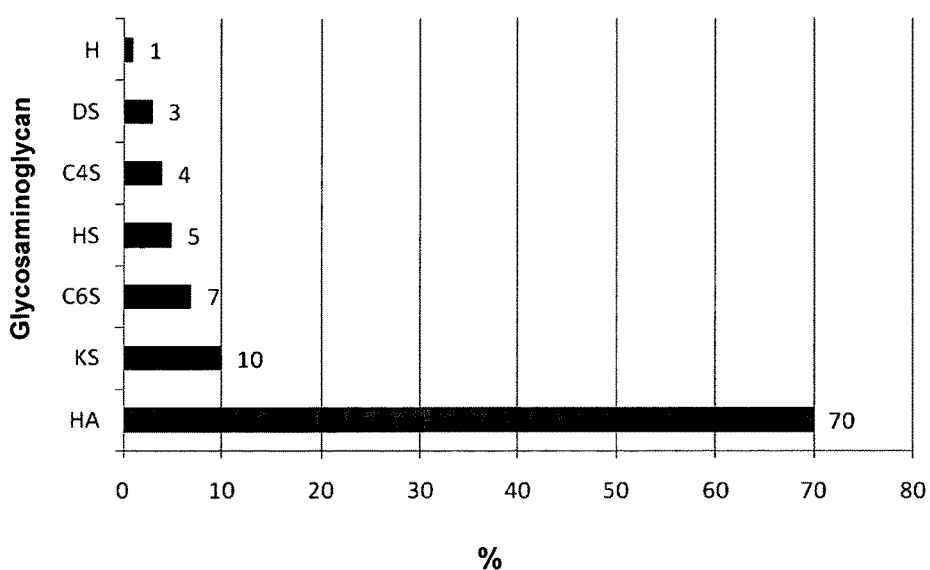
FIG. 1: Characterization and quantification of GAGs present in the biomaterial of the invention. The bar chart shows the different types of GAGs present in the biomaterial of the invention, as well as the compositional percent contribution of each. HA: hyaluronic acid, KS: keratan sulfate, C6S: chondroitin-6-sulfate, HS: heparan sulfate, C4S: chondroitin-4-sulfate, DS: dermatan sulfate, H: heparin.

The umbilical cord contains large amounts of (sulfated and non-sulfated) GAGs forming part of the soft connective tissue referred to as WJ. Among these GAGs, the main non-sulfated GAG is hyaluronic acid (Hadidian et al., 1948; Jeanloz et al., 1950), although smaller proportions of sulfated GAGs are also detected (Danishefsky et al., 1966). Furthermore, histological studies of the umbilical cord have suggested the presence of heparin (Moore et al., 1957). It is also very probable that the umbilical cord has more minor sulfated GAGs that have not been identified yet.

The present invention relates to an injectable hydrogel made up of the GAGs present exclusively in the WJ of the umbilical cord. This hydrogel is completely free of cells and any other vascular components present in the umbilical cord from which the biomaterial may be obtained, so that it has little to no immunogenicity. The biomaterial of the invention, either in its form combined with cells or alone, is useful for therapeutic and cosmetic treatments In the context of the present invention, the following terms are hereby defined:

"Hydrogel" refers to the formation of a colloid in which the disperse phase (colloid) has combined with the continuous phase (water) to produce a viscous jelly-like substance. The colloid is typically an interpenetrating network of hydrophilic filaments of synthetic or natural production.

"Injection" refers to the forcible insertion of a substance into a cavity. For example, a substance (usually of therapeutic value) is injected into a wound, or into the body cavity, circulation, or other location. For the purpose of the present invention, injection can consist of various modes of penetration into the desired location. For example, injection can involve hypodermic needles of gage sizes ranging from 0.5 mm to 15 mm. In arthroscopic or laparascopic surgery, a cylinder port, needle, or other similar object is used to treat internal pathologies. In this form of injection, a therapeutic agent such as a scaffold is forcibly passed through the access port which can have a considerably larger gage size than a hypodermic needle (e.g. 0.5 cm 4 cm).

"Injectable hydrogel" refers to the act of applying a hydrogel using an injection technique to a pathology that penetrates the barrier of the skin. For example, the pathology could be a chronic wound, a damaged organ, damaged tissue, or any other injury beneath the skin barrier necessitating treatment. Method of application can vary widely from hypodermic syringe to arthroscopic/laproscopic techniques to ad hoc devices designed specifically to apply materials to affected areas. For example, a caulk gun analog could be utilized to deliver a high-viscosity substance; a device that spools thread through a needle might be applied to deliver a filamentous polymerized hydrogel substance; a arthroscopic/laproscopic port might be utilized to deliver a hydrogel plug to a cartilaginous condyle defect. One experienced in the art can appreciate the multitudes of possibilities for injection techniques.

"Crosslinked hydrogel" refers to the ionic or covalent stabilization of a hydrogel that may or may not be reversible. Crosslinked hydrogels have higher viscosities than non-crosslinked hydrogels, are suitable for manipulation, possess stable three dimensional morphologies, and can be ruptured upon the application of mechanical force.

"Three dimensional hydrogel" refers to a crosslinked hydrogel that maintains a three dimensional form including stable finer three dimensional structures such as pores. In contrast, a non-crosslinked hydrogel with flow to fill any container in which it is placed. This resistance to flow in a crosslinked hydrogel is characteristic of the ability of a crosslinked hydrogel to maintain a stable three dimensional structure.

The origin of the umbilical cords from which the WJ is extracted for the purposes of the present invention can be sourced from mammalia including both animal and human. Additional potential sources of WJ are the umbilical cords of animals such as: cows, sheep, pigs, antelopes, camels, deer, goats, horses, elephants, rhinoceroses, hippopotamuses, giraffes, bison, buffalo, tigers, lions, leopards, bears, etc. The biomaterial is formed by a mixture of glycosaminoglycans selected from the group comprising: hyaluronic acid, keratan sulfate, chondroitin-6-sulfate, heparan sulfate, chondroitin-4-sulfate, dermatan sulfate and heparin.

The biomaterial is preferably found forming the following combination and proportion of the mixture of GAGs: hyaluronic acid (40-80%), keratan sulfate (2-25%), chondroitin-6-sulfate (3-10%), heparan sulfate (1-9%), chondroitin-4-sulfate (0.5-7%), dermatan sulfate (0.1-7%) and heparin (0.05-3%), more preferably the combination of GAGs is: hyaluronic acid (70%), keratan sulfate (10%), chondroitin-6-sulfate (7%), heparan sulfate (5%), chondroitin-4-sulfate (4%), dermatan sulfate (3%) and heparin (1%).

The present invention also relates to the biomaterial made up of the previously described hydrogel, which is optionally combined with cells for a compound therapeutic effect. The action of the hydrogel is thus enhanced in the regenerative and tissue repair process in severely damaged tissues or in tissues without the possibility of in situ cell recruitment by the patient, as a result of the fact that the biomaterial now contains healthy cells that can contribute to the effectiveness of the product. The cells added to the biomaterial scaffold to form the construct can be, among others: undifferentiated mesenchymal stem cells or mesenchymal stem cells differentiated into another cell strain, undifferentiated hematopoietic stem cells or hematopoietic stem cells differentiated into another cell strain, chondrocytes and chondroblasts, osteoblasts and osteocytes, keratinocytes, fibroblasts, myocytes, adipocytes, neurons or other cells from the nervous system, cells from the white blood cell system, corneal cells, endothelial cells or epithelial cells.

The following aspects related to the present invention are presented as follows: (i) obtaining an extract of GAGs from Wharton's jelly of the umbilical cord (ii) production of the GAG hydrogel isolated from Wharton's jelly of the umbilical cord (iii) characterizing the hydrogel obtained and (iv) uses of the hydrogel biomaterial. In addition, studies/examples follow that demonstrate the ability of injectable hydrogel to effect positive cell behavior and interactions when compared to hyaluronic acid (HA).

Obtaining an Extract of GAGs from the WJ of the Umbilical Cord.

The process for obtaining the biomaterial comprises the following steps:
   a. Obtaining a umbilical cord from animal or human origin;
   b. Treating the umbilical cord with a saline solution and antibiotics;
   c. Eliminating all the blood from the surface of the cord;
   d. Fragmenting the cord into sections of 1-2 cm;
   e. Cleaning out all the blood retained inside;
   f. Eliminating the umbilical cord membrane and blood vessels;
   g. Separating the gelatinous substance comprising Wharton's jelly;
   h. Enzymatically digesting the gelatinous substance obtained; and
   i. Precipitating and isolating the GAGs;

Specifically, the following is performed for isolating the glycosaminoglycans from the WJ of the umbilical cord:

Obtaining Wharton's Jelly.

The umbilical cord is collected immediately after the delivery and it is processed or maintained at 4° C. until processing. Not more than 24 hours in these conditions should elapse.

For processing, the umbilical cord is preferably maintained in sterile conditions in a biosafety level II laminar flow hood. It is subjected to at least three successive washings with a DMEM (Dulbecco's Modified Eagle's Medium) solution or with phosphate buffer 1× (1×PBS) with a mixture of antibiotics (penicillin, streptomycin, amphotericin-B) and/or an erythrocyte lysis buffer solution, to completely remove blood residues.

Once the surface of the umbilical cord is cleaned of blood, it is transferred to a Petri dish and fragmented into sections of 1-2 cm. When cutting the cord into fragments it is possible that blood retained inside the blood vessels of the umbilical cord is released, so it will be necessary in this case to thoroughly wash the cord fragments.

The umbilical cord has at the structural level two umbilical arteries and one umbilical vein, sustained by a consistent matrix which is WJ and covered with a thin membrane. In order to exclusively obtain the WJ, the membrane and blood vessels are mechanically removed. To do so, the umbilical cord fragments are longitudinally sectioned and with the aid of a scalpel and tweezers both the umbilical cord membrane and blood vessels are carefully removed. The gelatinous substance that is obtained as a consequence of this mechanical separation is the WJ. Generally between 20 and 160 g of Wharton's jelly are obtained from 25 to 200 g umbilical cord.

Extraction of GAGs from Wharton's Jelly.

The protocol described in the literature (Rogers et al., 2006) for obtaining GAGs from cartilage by means of enzymatic digestion with the enzyme papain from Papaya latex (SIGMA, Ref: P4762) was used, with some modifications, to obtain GAGs from the WJ of the umbilical cord. The WJ obtained in the previous point is immersed in 20 ml of the extraction buffer solution (5 mM cysteine, 100 mM $Na_2HPO_4$ buffer solution, 5 mM EDTA, 10 mg (14 U/mg) papain, pH 7.5) for 24-48 hours at 60° C. for complete digestion.

Once the WJ has been entirely digested, it is centrifuged to remove the useless digestion residue. At this point, it is observed that the digestion volume is greater than the starting volume. This increase is due to the dissolution of the GAGS present in the WJ and therefore to the release of the water that they accumulate.

Once the sample is centrifuged, the supernatant is transferred to another container and the GAGs present in the sample are then precipitated out.

Precipitation and Isolation of GAGs from the WJ of the Umbilical cord.

The GAGs of the WJ are precipitated out with 5 volumes of 100% ethanol. By means of this step, the GAGs of the sample as well as the salts present therein are precipitated out. The precipitation occurs due to the fact that the water molecules present in the sample interact with the ethanol molecules, such that the water molecules cannot interact with the GAGS of the sample, the latter becoming insoluble in water, and therefore precipitating out. Therefore, right after adding the ethanol and shaking the tube, a whitish precipitate is observed. The GAGs are left to precipitate for 12 hours at −20° C. Once precipitated out, they are centrifuged to remove the 100% ethanol and the precipitate is washed with 5 volumes of 75% ethanol to remove the possible residual salts that have precipitated out in the sample. The sample is centrifuged once again to completely remove the supernatant.

Once the sample of GAGs has precipitated, the residue is left to dry for at least 30 minutes at ambient temperature until all the ethanol has evaporated. Once the ethanol has evaporated, the sample of GAGs is resuspended in Milli-Q $H_2O$ and is stored at 4° C. until use. The Hydrogel thus obtained can be mixed with an injectable serum and or applied directly to the area to treat. Notwithstanding the above, the mechanical resistance of this type of material is low; it is not considered for bearing loads unless it is combined with a reinforcing material to form a composite. For example, a calcium phosphate support could serve as a reinforcing matrix within a composite material. In addition; there is a very high affinity among the polysaccharide molecules making up this injectable hydrogel. This affinity is apparent in the high cohesion of the hydrogel biomaterial. However, there is also a substantial adhesive character to the hydrogel which is beneficial to local isolation of the hydrogel where injected. Lastly, the versatility of the hydrogel dictates that it may be administered alone or in combination with cells.

There are other therapeutic applications which require a more resistant, stable and permanent injectable hydrogel biomaterial with an internal structure that better facilitates its colonization by cells from either the adjacent tissues in the application site or by specific cells arranged in the biomaterial prior to its implantation. In this case, the biomaterial of the present invention would act like a bioactive three-dimensional matrix to induce healing and repair of a tissue wound.

Hyaluronic acid, chondroitin-6- and -4-sulfate, keratan sulfate, dermatan sulfate, heparan sulfate and heparin regulate cell activity and activate the synthesis of a new extracellular matrix. The diversity and composition of GAGs present in the biomaterial allows the existence of a number of binding sites specific to growth factors regulating the cell proliferation and differentiation processes, as well as the cells' capacity for the synthesis of a new extracellular matrix and growth factors. This effect leads to a greater capacity for cellular response in the affected tissues and accelerates regeneration and even allows healing in the case of extremely degraded areas, as is the case of chronic ulcers.

A stabilization (crosslinking) strategy is required in order to facilitate applications where the biomaterial is to perform as a stable three dimensional scaffold. In order to achieve this objective, the GAGs can be chemically modified or crosslinked to form the injectable hydrogel of the present invention. These chemical modifications (crosslinking, polymerization) typically involve alcohol or carboxylic groups, and can occur in situ after injection, or prior to injection. In addition, this process involves the chains of a water-soluble polymer becoming insoluble (Elisseeff et al., 2005).

The injectable hydrogels obtained by means of crosslinking have unique properties making them potentially useful for tissue engineering: high water content for carrying nutrients or waste substances, elasticity and the capacity of encapsulating or immobilizing cells in situ in a 3D microenvironment. The crosslinking density directly affects the size of the pore of the injectable hydrogel and therefore the physical properties thereof, such as the water content or the mechanical resistance for example. An injectable hydrogel with a large crosslinking density and therefore a very small pore size will thus absorb less water and will have greater mechanical resistance than an injectable hydrogel with a lower degree of crosslinking and a large pore size.

The formation of crosslinked hydrogel for injection can be carried out by means of several methods including, but not limited to: temperature changes, chemical reactions and photopolymerization. Crosslinking can be carried out in situ following injection by standard hypodermic syringe methodologies or ex vivo prior to injection and thus utilizing techniques more akin to laparascopy/arthroscopy as defined earlier in this document.

In one embodiment of the present invention the crosslinking reaction is carried out as follows: an aqueous solution of the polymer to be crosslinked (in this case, an aqueous solution of GAGs) is obtained and the chemical reagent that will cause the crosslinking is added. In this case, to obtain the stabilized hydrogel, EDC (1-ethyl-3-(3-dimethylaminopropyl carbodiimide hydrochloride) is used because EDC activates carboxyl groups in aqueous solutions. These activated carboxyl groups are capable of reacting with primary amines or hydroxyl groups, resulting in amide or ester bonds. Once the hydrogel is formed, it is washed several times with PBS to remove the EDC residues that may remain. (Pieper et al., 1999; Wissink et al., 2001).

Figure 3:
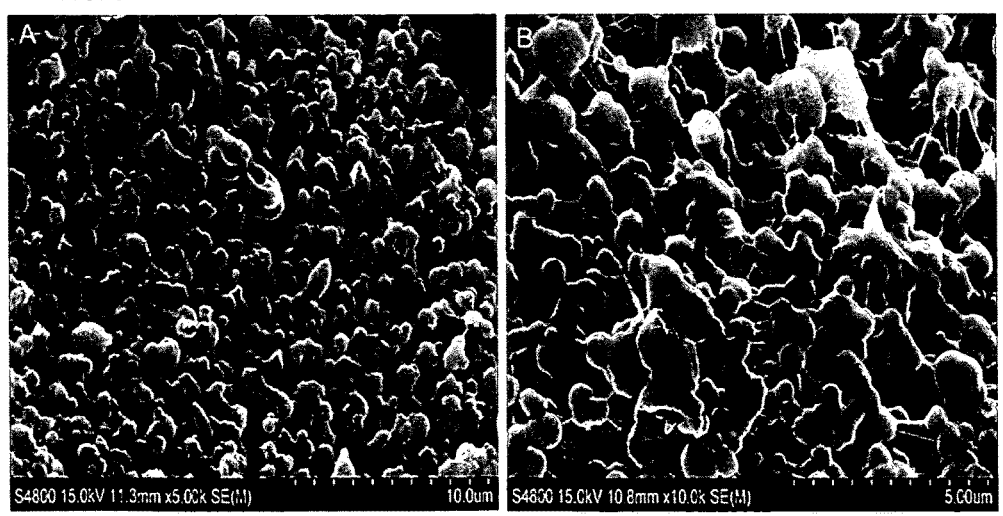
FIG. 3: Images of the internal three-dimensional structure of the biomaterial of the invention by scanning electron microscopy. The image shows the internal structure of the biomaterial of the invention at two different magnifications (A: 10 μm and B: 5 μm), in which the GAG units interconnected to one another can be seen, offering a very homogeneous porous structure.
Figure 5:
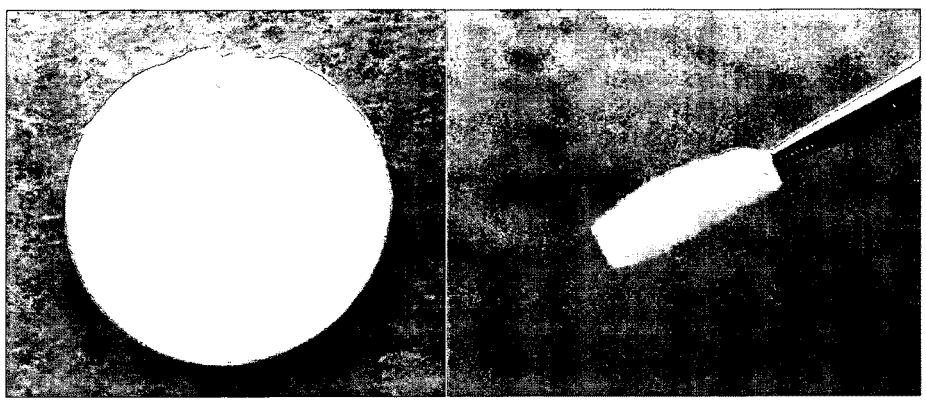
FIG. 5: Magnified image of the three-dimensional biomaterial. Shown is the macroscopic three-dimensional structure of the solid biomaterial of the invention after lyophilization for which a standard 24-well culture plate was used as a mold.

Optionally, the injectable hydrogel can solidify in a mold intended for such process during the crosslinking reaction, such that it takes the desired shape and size depending on the mold that is used. These hydrogels can be dried by means of the process referred to as lyophilization to thus obtain a porous structure due to the removal of the water molecules intercalated between the GAG molecules present in the hydrogel (FIG. 5). Furthermore, once the biomaterial is lyophilized, the three-dimensional structure of the hydrogel can be characterized by means of scanning electron microscopy (SEM) (FIG. 3). Once the hydrogel is obtained in its final shape, it is sterilized by means of exposure to ultraviolet radiation for a period of 40 minutes. The sterility tests conducted on the hydrogel demonstrated that the biomaterial was optimally sterilized. Additional techniques for sterilization could be ethylene oxide gas treatment or gamma irradiation as one knowledgeable in the art will realize.

Figure 4:
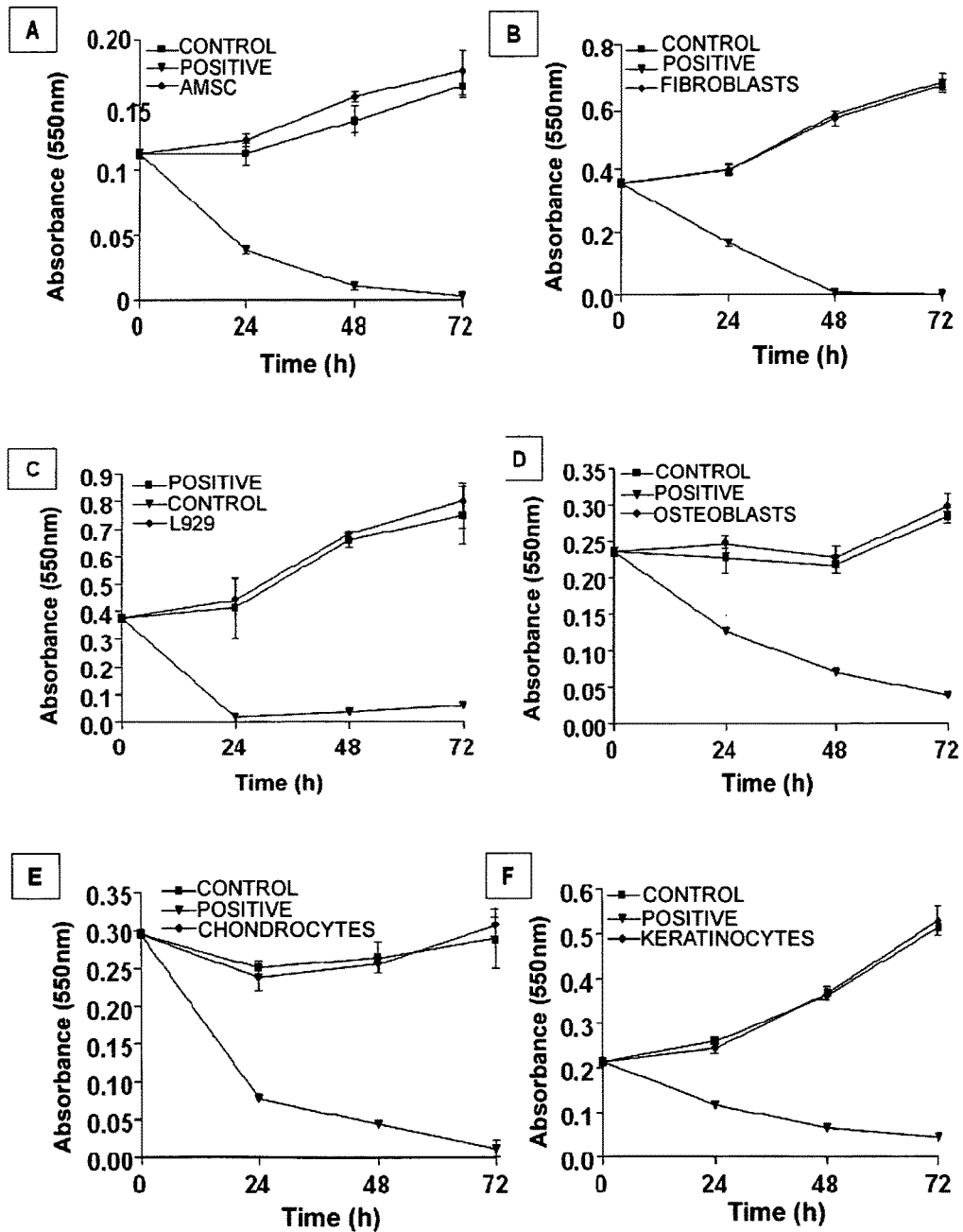
FIG. 4: Results of the toxicity study of the cells in the biomaterial of the invention. The graphs show the cytotoxicity curves of the AMSC cells (adipose-derived mesenchymal stem cells) (FIG. A), mouse fibroblasts (FIG. B9), L929 (FIG. C), osteoblasts (FIG. D), chondrocytes (FIG. E) and keratinocytes (FIG. F). The results are given with respect to a control (cells without biomaterial) and to a positive control (cells in a toxic biomaterial as determined according to ISO-10993 standard, PVC). As can be observed in the graphs, the biomaterial does not cause toxicity in any of the tested cell types, since the mitochondrial activity of the cells arranged on the biomaterial does not show differences with respect to the control cells (in standard culture conditions).

Once sterilized, the injectable hydrogel is ready to be used directly or in association with cells. Cell association assays with the hydrogel of the invention demonstrated that the biomaterial is not cytotoxic based on the results from proliferation capacity experiments (FIG. 4).

Uses of the Biogel.

The biomaterial of the invention, either in its form combined with cells or alone, can be applied in its injectable form in joint system diseases and in aesthetic treatments. The cells that can be used are, among others: undifferentiated mesenchymal stem cells or mesenchymal stem cells differentiated into another cell strain, undifferentiated hematopoietic stem cells or hematopoietic stem cells differentiated into another cell strain, chondrocytes and chondroblasts, osteoblasts and osteocytes, keratinocytes, fibroblasts, myocytes, adipocytes, neurons or other cells from the nervous system, cells from the white blood cell system, corneal cells, endothelial cells or epithelial cells.

Depending on the therapeutic or cosmetic application for which the hydrogel will be intended, the injection technique will be different and the viscosity of the hydrogel will be adapted to the caliber of the injection system.

The viscosity of the hydrogel of the present invention may range from 10 to 150,000 cS; in the case of non-crosslinked hydrogel is from 10 to 15,000 cS, preferably between 10 and 2,000 cS. The crosslinked hydrogel can have a viscosity ranging from 15,000 to 150,000 cS. The viscosity of the hydrogel can be modified by crosslinking according to needs.

TABLE 1

Viscosity values of various non-crosslinked and crosslinked hydrogels derived from Wharton's Jelly as described in the biomaterial of the present invention.

| Hydrogel | Viscosity (cS) |
| --- | --- |
| 5%-10% Human-/porcine-derived (CROSSLINKED) | 70,000 |
| 50% Human-/porcine-derived | 15,000 |
| 40% Human-/porcine-derived | 9,100 |
| 30% Human-/porcine-derived | 4,900 |

TABLE 1-continued

Viscosity values of various non-crosslinked and crosslinked hydrogels derived from Wharton's Jelly as described in the biomaterial of the present invention.

| Hydrogel | Viscosity (cS) |
|---|---|
| 20% Human-/porcine-derived | 2,000 |
| 10% Human-/porcine-derived | 150-580 |
| 5% Human-/porcine-derived | 19-58 |
| 1% Human-/porcine-derived | 4-6 |

The biomaterial developed in the present invention is useful in the following therapeutic and cosmetic treatments: remodeling, filling or reconstruction of soft tissues, the treatment of wrinkles, creases and scars, burns, ulcers, soft tissue augmentation, facial lipoatrophy, intervertebral disc diseases, repair of cartilage, musculoskeletal injuries, osteoarthritis and periarthritis; treatment of tumors, vaginal diseases, brain injuries, marrow repair, neurodegenerative disorders, cardiovascular diseases and lubricating processes, as an analgesic and anti-inflammatory.

The crosslinked injectable hydrogel of the invention can have a substantially porous structure. In one embodiment the pore diameter is 0.5-1,000 µm, preferably 0.5500 µm, with a viscosity greater than 15,000 cS. Said biomaterial can be applied preferably as a scaffold in the following pathologies: treatment of burns, ulcers and dermal-epidermal defects, treatment of ophthalmological diseases, such as corneal injuries, retinal injuries or cataracts; repair of cartilage, treatment of the osteoarticular system, as in the case of osteochondral defects, osteoarthritis or bone defects, and an adjuvant in the resolution of vaginal diseases, treatment of gingivitis and periodontitis; use in the development of cell culture systems.

The chondral diseases are an important socio-economic problem worldwide. In this sense, despite the difficulty of recording their incidence, it is estimated that joint injuries affect 500 million people.

Chondral pathologies occur as a result of injuries or diseases which, if they are not treated, can result in degenerative diseases such as the osteoarthritis (OA).

OA is one of the most common types of arthritis which affects 35-40 million people in the United States and Europe. It is a degenerative disease which causes the disintegration of cartilage accompanied by a reaction in the bones. It generally affects hands, knees, hips feet and the neck, and in adults, it is considered one of the most common causes of physical incapacitation.

Joint cartilage is a highly specialized avascular tissue which protects the bone of the diarthrodial joint from forces associated with weight and impacts which lead to frictions between the joint surfaces. This tissue is formed by a single cell type, chondrocytes, and by an important and rich extracellular matrix. Said matrix consists of a dense network of type II collagen fibers (predominant molecule), and, within this network, macro-aggregates of proteoglycans, which contain GAGs such as chondroitin sulfate, keratan sulfate, hyaluronic acid and aggrecan.

The specialized architecture of cartilage and its limited repair capacity make the treatment of this type of injuries very complicated. The absence of vascularization makes its regenerative capacity very limited since the stem cells cannot access the damaged area to contribute in the regenerative process.

In recent years, biodegradable biomaterials have been used for the treatment of chondral injuries. In this sense, macroscopic synthetic polymers (lactic acid, glycolic acid, caprolactone . . . ) have become the most important and numerous groups of biomaterials. However, these solid macroscopic materials require the use of aggressive surgical procedures, such as conventional surgery. For the purpose of overcoming these limitations, new biomatrixes that can be implanted by minimally invasive techniques, such as by injection or arthroscopy, are currently being developed.

Therefore, one of the applications of the injectable biomaterial of the present invention is the regeneration of the joint cartilage damaged in the degenerative processes of osteoarthritis. The biomaterial of the present invention can be easily administered in the area to be regenerated by means of percutaneous injection techniques such as arthroscopy, or by means of any injection device. In addition to the easy administration, the injectable hydrogel has the property of forming a stable implant which is fitted to the size and geometry of the deteriorated tissue.

Another application of the biomaterial of the present invention is in the treatment of wounds. Chronic diabetic, decubitus, and venous ulcers are an important problem that affects between 3 and 6 million of people in the United States. This pathology affects 1-3% of the population of developed countries and 15% of the patients admitted in hospitals suffer this condition. The large number of patients suffering these injuries produces considerable socio-economic and healthcare repercussions, a high treatment cost thus being established, and the quality of life of the patient being considerably altered.

Ulcers are traumas that have a profound effect on the organism with a considerably complex physiopathology. A complex synergistic interaction occurs between fibroblasts (cells of the dermis), keratinocytes (cells of the epidermis), extracellular matrix, and plasma-derived proteins in the wound bed. Progression through the different wound healing phases: hemostasis, inflammation, repair, and remodeling, is typical, but the chronic nature and recurrence of these wounds is of clinical importance. Despite the large variety of treatments and scaffolds available today, the healing efficacy and healing rate continue to be extremely low, therefore necessitating more effective treatments that can achieve rapid wound healing. The progressive knowledge gained on the physiopathology of chronic ulcers in recent years has facilitated the generation and development of new scaffolds that are significant advancements in the treatment of this disease. Although until now, there is no ideal scaffold for covering the skin; said scaffold must comply with a series of basic characteristics such as: 1) fast adhesion to the wound, 2) providing an effective barrier function against the loss of fluids, 3) mechanical resiliency and long-term stability, 4) easy to sterilize, 5) easy to handle and transport, and 6) they must be innocuous.

In summary, the biomaterial of the present invention has most of the characteristics necessary for a scaffold or a diluent to be effective in treating the mentioned diseases. In this sense, for the purpose of evaluating the therapeutic effect of the present biomaterials in vivo experimental studies have been carried out, as described in examples 9 and 10.

EXAMPLES

Example 1. Obtaining Wharton's Jelly

The following example was performed with both human- and porcine-sourced umbilical cords. To isolate the GAGs from the WJ of the respective umbilical cords, the procedure below was followed.

In each case, a 50 g umbilical cord was collected immediately after delivery in a sterile bottle in which 300 ml of PBS at 1× concentration (for 1 liter of $H_2O$: 8 g NaCl, 0.2 g KCl, 1.44 g $Na_2HPO_4$, 0.24 g $KH_2PO_4$, pH-7.4 in 1 L of $H_2O$) and 3 ml of a mixture of antibiotics of penicillin (30,000 units), streptomycin (30,000 µg) and amphotericin-B (75 µg) (LONZA, Ref: 17-745E) at 1× concentration, had previously been deposited. The umbilical cords can be stored at 4° C. for not more than 24 hours until processing, but in this example the umbilical cords were processed immediately after they were received.

For processing, the umbilical cords were maintained in sterile conditions in a biosafety level II laminar flow hood and were subjected to successive washings to completely remove the blood residues they contain. To that end, they were placed in two containers, where 300 ml of 1×PBS (for 1 liter of $H_2O$: 8 g NaCl, 0.2 g KCl, 1.44 g $Na_2HPO_4$, 0.24 g $KH_2PO_4$, pH-7.4 in 1 L of $H_2O$) containing 3 ml of a mixture of antibiotics of penicillin (30,000 units), streptomycin (30,000 µg) and amphotericin-B (75 µg) (LONZA, Ref: 17-745 E) were added; they were manually shaken by vertically tilting the bottle 5 times for 10 seconds, and the liquid was discarded, this operation being repeated at least 3 times until most of the blood was removed. Then the umbilical cords were washed with 500 ml of an erythrocyte lysis solution at 1× concentration (for 1 liter of $H_2O$: 8.99 g $NH_4Cl$, 1 g $KHCO_3$, 37 mg EDTA, pH 7.3) until the complete removal of blood residues.

Once the surface of the umbilical cords was cleaned of blood, they were transferred to a 10 cm Petri dish and were cut up with sterile scissors into 1-2 cm fragments. Since blood retained in the blood vessels was released while cutting the umbilical cords into fragments, 10 ml of 1×PBS containing 1 ml of a mixture of antibiotics (10,000 units), streptomycin (10,000 µg) and amphotericin-B (25 µg) were added to thoroughly clean said fragments, and the surface of the fragment was pressed against its support surface, making horizontal shifting movements along the fragment with a sterile scalpel. This process was repeated until all the blood residues were removed from the interior. The completely clean umbilical cord fragments were transferred to a sterile tube and were immediately processed, although if needed, they can be indefinitely cryopreserved at −80° C.

The membrane surrounding the umbilical cords and the blood vessels located therein were then mechanically removed. To do so, the pieces of umbilical cord were longitudinally opened and with the aid of a scalpel and tweezers both the umbilical cord membrane and blood vessels were carefully removed. The gelatinous substance that was obtained as a consequence of this mechanical separation is the WJ. 25 g of WJ were obtained.

Example 2. Extraction of GAGs from Wharton's Jelly

The following example was performed with both human- and porcine-sourced umbilical cords. A protocol described to obtain GAGs from human cartilage was utilized, with some modifications, to obtain GAGS from the WJ of the umbilical cord (Rogers et al., 2006).

Both WJ obtained in Example 1 were immersed in 20 ml of the extraction buffer solution (242 µl of 200 mM L-cysteine, 1.42 ml of 704 mM $Na_2HPO_4$ buffer, 100 µl of 0.5 M EDTA, 10 mg (14 U/mg), pH 7.5) papain (SIGMA, Ref: P4762) and they were maintained at 60° C. for 12 hours to completely digest the WJ, and once they were digested, the samples were centrifuged at 1,500 g for 5 minutes to remove the digestion residue. It was observed that the digestion volumes were approximately 30 ml, approximately 10 ml more than the starting volume of 20 ml, due to the dissolution of the GAGs present in the WJ and therefore due to the release of the water that these had accumulated.

Once the samples were centrifuged, the supernatant was transferred to another tube and the GAGs present in the samples were then precipitated out.

Example 3. Precipitation and Isolation of GAGs from the WJ of the Umbilical Cord The GAGs of the WJ present in the supernatant of example 2 were precipitated out with 5 volumes of 100% ethanol. By means of this step, the GAGs of the samples as well as salts present therein were precipitated out. This is due to the fact that the water molecules present in the samples interact with the ethanol molecules, such that the water molecules cannot interact with the GAGs of the samples. The GAGs were left to precipitate for 12 hours at −20° C. Once precipitated out, they were centrifuged at 1,500 g for 5 minutes, all the 100% ethanol thus being removed. The precipitate was washed with 5 volumes of 75% ethanol to remove the possible residual salts that may have precipitated out in the sample. Then it was centrifuged about 5 minutes at 1,500 g and the supernatant was completely removed.

Once the samples have precipitated, the solid residue was left to dry for about 30 minutes at ambient temperature until all the ethanol had evaporated. The amount of GAGs that precipitate out starting from a sample of about 25 g of WJ can range between 50 and 300 mg, depending on the starting material. In these specific cases, approximately 250 mg GAG precipitate was obtained. To obtain the hydrogel of the present invention, the GAG precipitates were resuspended in 1 ml of Milli-Q $H_2O$ and stored at 4° C.

Example 4. Production of an Injectable Hydrogel Containing GAGs of the WJ of the Umbilical Cord The water content of the hydrogel can be from 10% to 100 times its own weight, depending on the viscosity required for its application.

The hydrogel obtained after resuspension of the GAGs precipitated in 1 ml of $H_2O$ was resuspended in an injectable physiological serum solution and was left stirring moderately in a vortex until complete dissolution and homogenization occurred. Once the hydrogel was dissolved, it was stored at 4° C.

Example 5. Production of a Crosslinked Hydrogel Containing GAGs from the WJ of the Umbilical Cord To produce a more consistent and stable hydrogel, the process described in the literature was followed (Cui et al., 2006). An aqueous solution was prepared from the extracts of GAGs obtained from the NJ according to Example 3. Specifically, a solution of GAGs in $H_2O$ at 1% was prepared. To that end, 10 ml of $H_2O$ were added to the 200 mg of GAGs obtained after their precipitation and isolation (Example 3). 1.2 g of adipic dihydrazide (ADH) were added to the solution and the pH of the solution was adjusted to pH=3.5 with 0.1 N HCl. Once this pH was adjusted, 0.6 g of the fixative, EDC (1-ethyl-3-(3-dimethylaminopropyl carbodiimide hydrochloride) (SIGMA, Ref: E6383), was added to the solution. The mixture was maintained between 30 minutes and 1 hour under constant stirring at ambient temperature until the stable hydrogel was obtained.

Once the stable hydrogel was formed, it was washed 3 times with 1×PBS (for 1 liter of H$_2$O: 8 g NaCl, 0.2 g KCl, 1.44 g Na$_2$HPO$_4$, 0.24 g KH$_2$PO$_4$, pH=7.4 in 1 L of H$_2$O) 5 minutes each time to remove the EDC excess. With respect to the physical shape of the hydrogel, it will have the shape of the mold in which it solidifies, such that standard 96, 48, 24, 12 and 6-well culture plates, Petri dishes or any other container with the desired shape can be used.

Additionally, the hydrogel can be solidified in a large container such as a beaker, and once it is solidified, the hydrogel can be cut with characteristic shape and thickness. Specifically, in this example the hydrogel solidified in wells of 24-well plates and once solidified it was washed 3 times for 5 minutes with 500 µl of 1×PBS.

In this case, the hydrogel crosslinked in 24-well plates was lyophilized according to standard techniques.

In this example, the three-dimensional structure of the hydrogel was analysed by means of scanning electron microscopy (SEM). Once the hydrogel was lyophilized the following was performed: a section of the lyophilized hydrogel was cut and this section was dried to the critical point with CO$_2$ in an AUTOSAMDRI-814 dryer and metalized with gold in a SPUTTER. The preparations were observed at a voltage of 20 KV in the JEUL scanning electron microscope (JSM35).

The SEM analysis (FIG. 3) of the dehydrated hydrogel indicated that it has a uniform porous structure. The micrograph shows the existence of a highly porous three-dimensional structure, with a pore diameter ranging between 0.5 and 500 µm. This range of pores involves the existence of micro- and macroporosity. The macropores (300-500 µm) are necessary so that suitable cell colonization is carried out, so that a high number of cells are concentrated and so that different cell types coexist, favoring the formation of structured tissues, for example, so that a vascular network can be formed. The intermediate pores allow cell integration. The micropores (0.5-50 µm) are necessary for cell survival, since they are responsible for carrying out the correct diffusion of gases, nutrients and the removal of the waste products resulting from cell metabolism. The pore size is measured based on the metric scale obtained by means of the scanning electron microscope.

This biomaterial shows a higher structural sensitivity, being indicated for applications in which not only is a bioactive nature and trophic action sought, but also a structure which can temporarily house cells until the tissue repair is performed, such as the treatment of ulcers and other dermal-epidermal diseases, the repair of cartilage and ophthalmological treatments, among others. The cells contained in the biomaterial can be those of the tissues adjacent to the implantation site which have managed to colonize it, or also cells arranged ex vivo in the biomaterial prior to its clinical application, such that its regenerative action is enhanced.

This biomaterial has a homogeneous distribution of pores with a size in a range of 0.5-1000 microns, determined by means of scanning electron microscopy techniques. This porosity range is suitable both for the diffusion of gases and nutrients through its entire structure, and for allowing cells to colonize.

Example 6. Characterization and Quantification of GAGs Present in the Biomaterial of the Invention The different GAGs present in the biomaterial of the invention were analyzed and quantified by means of the mass spectrometry (ESI/MS) technique. Given that by means of this technique only molecules with a molecular weight of between 200 and 2,000 Daltons can be determined and that the GAG molecules exceed this range for the most part, first, the sample was enzymatically digested in order to thus obtain GAG chains with a molecular weight between 200 and 2,000 Da.

As a standard for the identification and quantification of the GAGs, standard commercial compounds representing each GAG with a known concentration were used. Specifically, the standards used to perform the quantification of GAGs were the following: for hyaluronic acid:hyaluronic acid potassium salt (SIGMA, Ref: 53750); for chondroitin sulfate: chondroitin sulfate sodium salt (SIGMA, Ref: C4384); for dermatan sulfate: dermatan sulfate sodium salt (SIGMA, Ref: C3788); for keratan sulfate; keratan sulfate (CHEMOS, Ref: 7295); for heparin: heparin sodium salt (SIGMA, Ref: H8537); and for heparan sulfate: heparan sulfate sodium salt (SIGMA, Ref 51541).

The values of the quantification of GAGs present in the sample were obtained based on the results obtained for each GAG standard used.

In order to perform the enzymatic digestion of the GAGs, the process described in the literature was followed (Mahoney et al., 2001). To that end, the enzymes specific for the digestion of each GAG were used.

For hyaluronic acid, hyaluronidase (SIGMA, Ref: H3506) was used; for chondroitin sulfate, chondroitinase (SIGMA, Ref: C2780) was used; for dermatan sulfate, chondroitinase B (SIGMA, Ref: C8058) was used; for heparin, heparinase I (SIGMA, Ref: H2519) was used; for heparan sulfate, heparinase I (SIGMA, Ref: H2519) was used; for keratan sulfate, keratanase (K2876) was used.

These enzymes were prepared by resuspending 440 U of the corresponding enzyme in 10 ml of the following buffer: 2 ml of 100 mM phosphate buffer pH=7.77, 770 µl of 1 M NaCl, 1 mg of BSA and 7.23 ml of H$_2$O.

The enzymatic digestion buffer with an enzyme concentration of 160 U/ml was prepared as follows: 4.5 ml of enzyme (2000 U) were added to 7.5 ml of digestion buffer, 1.5 ml of 1 M NaCl, 0.333 ml of 3 M sodium acetate pH=5.2 and 5.67 ml of H$_2$O. The samples and the standards to be subjected to enzymatic digestion were prepared as follows: 500 µl of digestion buffer (80 U of enzyme) were added to 500 µl of standard for each GAG at a concentration of 2 mg/ml, such that the final solution of the standard was at a concentration of 1 mg/ml. The same was done with the sample of GAGs: 500 µl of digestion buffer (80 U of enzyme) were added to 500 µl of the sample of GAGs.

The samples were digested at 37° C. for 1 hour, after which the enzyme was inactivated by means of thermal denaturation at 60° C. for 5 minutes.

Once the digestions were done, the samples and the standards were analyzed by means of mass spectrometry. Mass spectrometry is an experimental methodology used to determine the mass-to-charge ratio of certain ions present in the sample to be analyzed. The mass spectrometer consists of 3 basic components: ion source, mass analyzer and detector. The sample to be analyzed is ionized by means of the ion sources, they are separated in the mass analyzer and are detected to produce a mass spectrum, in which the mass-to-charge values are shown compared to the relative abundance of a specific ion species.

Specifically, in this example the injection of samples in the mass spectrometer was carried out as follows: 20 µl of the samples were injected at a flow rate of 0.2 ml/minute directly into the mass/mass detector (Thermo LCQ model).

The negative electrospray ionization (ESI/MS) method was used and the time of the chromatogram was set at 10 minutes. The molecular ions with a range of ±6 Da, corresponding, according to the literature (Mahoney at al., 2001), to the molecular weight of recognized chains for each type of GAG, were selected. Said ions remained present both in the sample of standard GAGs and in the sample to be analyzed, so the presence of each GAG in the sample was thus qualitatively demonstrated. To ensure the reproducibility of the results, the samples and the standards were injected in duplicate.

For the quantification of the different GAGs, a standard line was made for the standard for each GAG at 1 mg/ml. The standard line made consisted of the following concentrations of each of the standard GAGs (hyaluronic acid, chondroitin sulfate, dermatan sulfate, heparin, heparan sulfate and keratan sulfate) used to make the standard lines: 750 µg/ml, 500 µg/ml, 250 µg/ml, 100 µg/ml, and 0 µg/ml. The dilutions of the standard line were carried out with $H_2O$ and a mixture containing equal proportions of enzymatic digestion buffer and $H_2O$ was used as the blank of the line.

The results of the qualification and the proportions of each GAG in the biomaterial of the invention are the following, taking into account that the origin of the biomaterial is natural, which implies the existence of variations in their composition (FIG. 1):
70% hyaluronic acid
10% keratan Sulfate
7% chondroitin-6-sulfate
5% heparan sulfate
4% chondroitin-4-sulfate
3% dermatan sulfate
1% heparin Example 7. Histological Study for Determining the Presence of Cell Remnants in the Biomaterial The biomaterial of the invention contains a combination of GAGs of a natural origin. This natural origin enhances their regenerative effect and their effect on cell activity, since the structures of the GAGs and the interactions between them are similar to how they are found in the extracellular matrix in physiological conditions.

Figure 2:
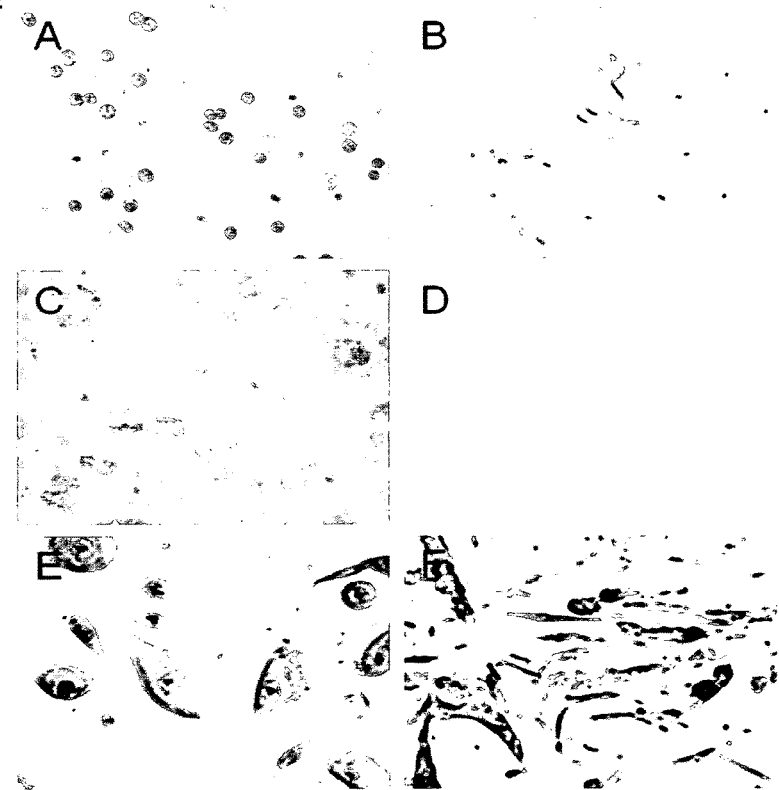
FIG. 2: Verification of the presence of GAGs in the sample and of the apparent lack of cells and DNA/RNA therein by means of histological staining. The images on the left show the samples with cells and the images on the right show the staining of the biomaterial alone. A, B: hematoxylin-eosin stain; C, D: methyl green-pyronin stain; E, F: alcian blue stain.

The umbilical cord is a type of tissue that possesses little to no immunogenicity, in fact, the heterologous use of the stem cells contained in the WJ is considered for treatments in a number of works. There are also works in which artery or vein systems are developed from the vasculature of the umbilical cord, also for heterologous use. However, to ensure that the biomaterial of the invention is free of cells and of cell remnants, which can cause inflammatory reactions or implant rejection reactions, hematoxylin-eosin, alcian blue and methyl green-pyronin histological stains have been performed (FIG. 2).

Hematoxylin-eosin: this is the histochemical stain most widely used on a histopathological level. It allows observing cells and cell components. Hematoxylin presents affinity for the acid components of the cell, especially nucleic acids, and eosin presents affinity for the basic areas, allowing a good observation of the cell cytoplasm. Preparations of the sample of GAGs (FIG. 2 B) were stained and extensions of cells were used as positive control (FIG. 2 A).

The process which was carried out to perform hematoxylin-eosin staining was the following: a sample of GAG was extended on a slide with the aid of a sterile swab, and the extension was left to dry at least 24 hours. Once the slides were dry, the extensions were fixed with 70% methanol for 5 minutes. After this time, the fixative was removed by washing with $H_2O$. The slides were stained with hematoxylin for 3 minutes (PANREAC, DC Harris hematoxylin solution). After this time, the excess dye was removed by washing with $H_2O$. All the slides were passed through $H_2O$ with 0.5% HCl to eliminate unspecific bonds of the dye. The slides were washed with $H_2O$. The slides were stained with eosin (0.5% in $H_2O$) for 30 seconds. The slides were washed with $H_2O$ to remove the eosin excess. Several drops of the Fluoromount-G mounting medium (SOUTHERN BIOTECH, Ref: 0100-01) were added to the preparation, they were covered with a slide cover and observed under a microscope.

The results of the stain with hematoxylin-eosin (FIG. 2, images A and B) indicate the absence of cells in the sample of analyzed GAGs.

Alcian blue: Alcian blue is one of the major cationic dyes (it contains positive charges in its molecule), which bind to sites with negative charges of the polysaccharides with sulfate, phosphate or carbonate radicals forming part of proteoglycans. These electrostatic bonds depend on the pH of the medium; at a neutral pH the dye binds to proteoglycans with neutral radicals; at acid pH it binds to sulfated proteoglycans; and at basic pH it binds to phosphate proteoglycans. At pH=1, alcian blue binds to weak and strongly sulfated proteoglycans, which contain chondroitin sulfate, dermatan sulfate, heparan sulfate and keratan sulfate forming part of the GAG of Wharton's jelly. Preparations of the sample of GAGs (FIG. 2 F) were stained and extensions of cells were used as control (FIG. 2 E).

The process that was carried out to perform the alcian blue staining in this example in particular was the following:

A sample of GAG was extended on a slide with the aid of a sterile swab, and the extension was left to dry at least 24 hours. Once the slides were dry, the extensions were fixed with 70% methanol for 5 minutes. After this time, the fixative was removed by washing with 1×PBS. The slides were immersed in 0.1 N HCl pH=1 for 5 minutes. After this time they were stained with 1% alcian blue in 0.1 N HCl pH=1 for 2 hours. The slides were immersed in 0.1 N HCl for 5 minutes and were immediately washed with $H_2O$ to remove the excess dye. Several drops of the Fluoromount-G mounting medium (SOUTHERN BIOTECH, Ref: 0100-01) were added to the preparations, they were covered with a slide cover and observed under a microscope. The results of the stain with alcian blue (FIG. 2, images E and F) indicate the presence of GAGs in the analyzed sample of biomaterial.

Methyl green-pyronin: This stain is used for the histological investigation of the nucleic acid contained in tissues, as well as to demonstrate the presence of lymphatic cells and plasma cells. It is also useful in the identification of plasma cells and RNA in tissue sections and cytological preparations. The pyronin stains the cytoplasm of the plasma cells and most of the nucleoli red. The methyl green stains DNA a bluish-green (purplish) color. Preparations of the sample of GAGs were stained (FIG. 2 D) and extensions of cells were used as control (FIG. 2 C).

The process which was carried out to perform methyl green-pyronin staining in this example in particular was the following:

A sample of each GAG was extended on a slide with the aid of a sterile swab, and the extension was left to dry at least 24 hours. Once the slides were dry, the extensions were fixed with 70% methanol for 5 minutes. After this time, the fixative was removed by washing with $H_2O$. The slides were immersed in 0.1 N HCl pH=1 for 5 minutes. After this time they were stained with methyl green-pyronin for 5 minutes (0.012% methyl green in $H_2O$, 0.01% pyronin in $H_2O$, 0.75% methanol) and were immediately washed with $H_2O$ to remove the excess dye. Several drops of the Fluoromount-G mounting medium (SOUTHERN BIOTECH, Ref: 0100-01) were added to the preparations, they were covered with a slide cover and observed under a microscope. The results of the stain with methyl green-pyronin (FIG. 2, images C and D) suggest the absence of nucleic acids in the analyzed sample of GAGs.

Example 8. Cytotoxicity Testing with Several Cell Types on the Biomaterial of the Invention The main requirement for a biomaterial to be able to be used for implantation or as a matrix for tissue engineering is the absence of cytotoxicity.

In order to verify that the biomaterial of the invention does not cause toxic effects, the cytotoxicity was determined by means of the MTT method (Roche Diagnostics, USA), validated by the ECVAM (European Centre for the Validation of Alternative Methods) on the cells arranged on the biomaterial of the invention. The cell types used are associated with the pathologies at which the biomaterial is targeted, such as, skin keratinocytes and fibroblasts, bone osteoblasts, cartilage chondrocytes and adipose-derived mesenchymal stem cells, as well as the cell line indicated in ISO 10993 for L929 toxicity assays.

The assay MTT is based on the capacity of the mitochondrial enzymes of the live cells to transform certain substrates into other secondary metabolites. The amount of compound formed depends on the activity of the mitochondrial dehydrogenase, which is a clear indicator of the number of viable cells existing in the culture.

Specifically, this mitochondrial test, Cell Proliferation Kit I (MTT) Cat. No. 1 465 007 Roche, determines the transformation carried out by the cell mitochondrial dehydrogenase succinates of (yellow) tetrazolium salt into insoluble (blue) formazan crystals. The cells were subsequently permeabilized and the crystals formed are solubilized, leading to a colored solution that can be quantified by measuring its absorbance in an ELISA microplate reader at a wavelength of 550 nm. The results obtained are shown in FIG. 4.

The process to be followed is the following:

1. The cells were seeded in a 96-well plates with 50 µl of biomaterial in each well at a density of 2,000-5,000 cells/well depending on the cell type. The suitable cell concentration for each cell type has been previously determined. The fibroblasts, osteoblasts, chondrocytes and adipose-derived mesenchymal stem cells, all from a primary culture of human origin, were seeded at a concentration of 4,000 cells per well, the L929 mouse fibroblast line was seeded at a concentration of 200 cells per well and the keratinocytes obtained from human skin in primary culture were seeded at a concentration of 5,000 cells per well.

2. The culture was left to stabilize at 37° C. and 5% $CO_2$ for hours before initiating the cytotoxicity assays. This assay included positive controls (cells+medium+known material which induces cytotoxicity, in this case polyvinyl polychloride or PVC was used), control (cells+standard culture medium), and cells in contact with the biomaterial of the invention.

3. The cells were allowed to incubate at 37° C. in the incubator for the time period indicated in the protocol until conducting the determinations, which in this case were at 24, 48 and 72 hours of contact.

4. After the incubation period ended, 10 µl of the MTT solution (0.5 mg/ml) were added to the culture in each well for each 100 µl of medium, and it was incubated for 4 hours at 37° C. in the incubator.

5. After incubation ended, the formazan crystals inside the cells could be observed. 100 µl of the solubilizing solution is added to each culture or well and it is incubated at 37° C. in the incubator overnight. The cells were thus permeabilized and the crystals thus solubilized with the 100 µl of solubilizer as indicated, leading to a readily quantifiable colored solution.

6. Once the crystals were solubilized, the culture plate is read directly with an ELISA reader at 550 nm. Before the reading, it is advisable to clean the lower surface of the plate with ethanol. As can be observed in FIG. 4, the biomaterial of the invention did not cause toxic effects on any of the tested cell lines, there being no significant differences with respect to the control.

Example 9. Use of the Biomaterial of the Invention in its Injectable Form for the Treatment of Osteoarthritis For the in vivo evaluation of the therapeutic effect of the biomaterial of the invention in osteoarthritis (OA), the hydrogel obtained in Example 3 was used and it was resuspended in an injectable physiological serum solution containing allogenic, cartilage-derived chondrocytes. Rabbits that were subjected to resection of the anterior cruciate ligament in one of their knees were used as an experimental model. This resection of the ligament was done by means of lateral arthrotomy. Next, for the purpose of destabilizing the knee, a period ranging from months to weeks was waited, during which time erosions in the cartilage similar to osteoarthritis occurred. In addition, animals without arthrotomy in the knee were used as a control group.

The wounded joint surface was prepared by means of washing and debridement by arthroscopic surgery and the injuries were covered with the injectable cell/biomaterial of the invention-mixture. Four weeks after depositing the biomaterial, the animals were sacrificed and the cartilage was extracted. The cartilage obtained was fixed in 4% paraformaldehyde for its subsequent histological processing. To obtain the histological sections, the sample was included in paraffin, for which purpose it was maintained for 5 minutes in alcohols at 50, 70, 90 and 100%. The samples were subsequently placed in citrosol for 5 minutes and were included in paraffin until obtaining a solid block. 5 µm histological sections were obtained using a microtome and the histological staining and immunolabeling were performed using these sections.

Different markers of the extracellular matrix of the cartilage were analyzed in the histological sections by means of immunohistochemical techniques. The specific molecules of the extracellular matrix of the cartilage and molecular markers studied were type I and type II collagen, aggrecan and versican. The immunolabeling was performed using monoclonal antibodies. The technique used for labeling the tissue section was direct immunolabeling, using monoclonal antibodies labeled with a fluorochrome. The labeling was observed using confocal microscopy.

The results obtained demonstrated that the biomaterial/cell combination induced the regeneration of the wounded cartilage since:

The injectable biomaterial and its cell component did not cause toxicity once implanted, i.e., inflammation phenomena were not observed at the macroscopic or microscopic level in the histological sections.

The biomaterial fit the geometry and size of the wound to be repaired and stayed in the area of the implantation. Alterations in the phenotype of the cells of the healthy tissue next to the area of the implant were not observed.

The presence of extracellular matrix molecules specific for cartilage, such as type II collagen, in the area of the implant indicated the start of the regenerative process with the formation of new extracellular matrix of the same quality as that of the native tissue.

These facts demonstrate that the biomaterial of the invention, combined with a cell therapy, promotes the regeneration of the chondral defect, unlike in the control animals which did not present any sign of cartilage repair.

Example 10. Use of the Three Dimensional Biomaterial

The solid biomaterial of the invention obtained in Example 5 has most of the characteristics necessary for a dressing to be effective in curing a chronic ulcer. In this sense, for the purpose of evaluating the therapeutic effect in chronic ulcers, the in vivo experimental study has been carried out using Swiss albino mice that were subjected to a thermal abrasion of about 3 cm$^2$ in the dorsal area. The control group consisted of animals subjected to this same type of wound but treated with a commercial hyaluronic acid gel.

For the application of the biomaterial of the invention, the surface of the induced wound was prepared by means of washing, disinfection and surgical debridement. The biomaterial was then applied to the wound via injection, where it covered and filled both in depth and superficially the affected area. 15 days after placing the biomaterial, the animals were sacrificed and the area of the wound was extirpated and fixed in 4% paraformaldehyde for its subsequent histological examination. For the processing, the sample was included in paraffin, for which purpose it was maintained for 5 minutes in alcohols at 50, 70, 90 and 100%. The samples were subsequently placed in citrosol for 5 minutes and were included in paraffin until obtaining a solid block. 5 µm histological sections were obtained using a microtome and the histological staining and immunolabeling were performed using these sections.

Different epidermal phenotype markers, such as 5 and 10 keratin, differentiation markers, such as involucrin and loricrin, the dermal marker vimentin, and components of the matrix such as laminin, were analyzed in the histological sections by means of immunohistochemical techniques. The technique used for labeling the tissue section was direct immunolabeling, using monoclonal antibodies labeled with a fluorochrome. The labeling was observed using confocal microscopy.

The results obtained demonstrated that the biomaterial was effective in the regeneration of the ulcer since:

The biomaterial applied in the wound was immunologically inert and no signs of toxicity were presented.

The biomaterial fit the geometry and size of the wound to be repaired, completely covering the affected area both in depth and superficially.

As the healing process progresses, the biomaterial degraded and was replaced with dermal-epithelial components.

The histological sections showed that the biomaterial induced the migration and proliferation of fibroblasts and keratinocytes, which remained viable therein.

The biomaterial of the invention induced healing of the wound that was twice as effective with respect to the control animals, and furthermore the quality of the new scar tissue was significantly greater than that in the animals without the application of the biomaterial of the invention.

Example 11. Viability and Metabolic Activity of Articular Cartilage Cells and Mesenchymal Stem Cells (MSC) in Co-Culture in the Injectable Form of the Biomaterial of the Present Invention To determine the viability and metabolic activity $2 \times 10^6$ cells were cultured in 800 µl of 10 mg/ml of the biomaterial of the present invention in 24 well plates. Chondrocyte and MSCs were maintained in culture for 7 days. At days 3 and 7, staining was performed with MTT vital dye, which stains the cells that are metabolically active, thus a measure of cell viability is obtained.

Figure 6:
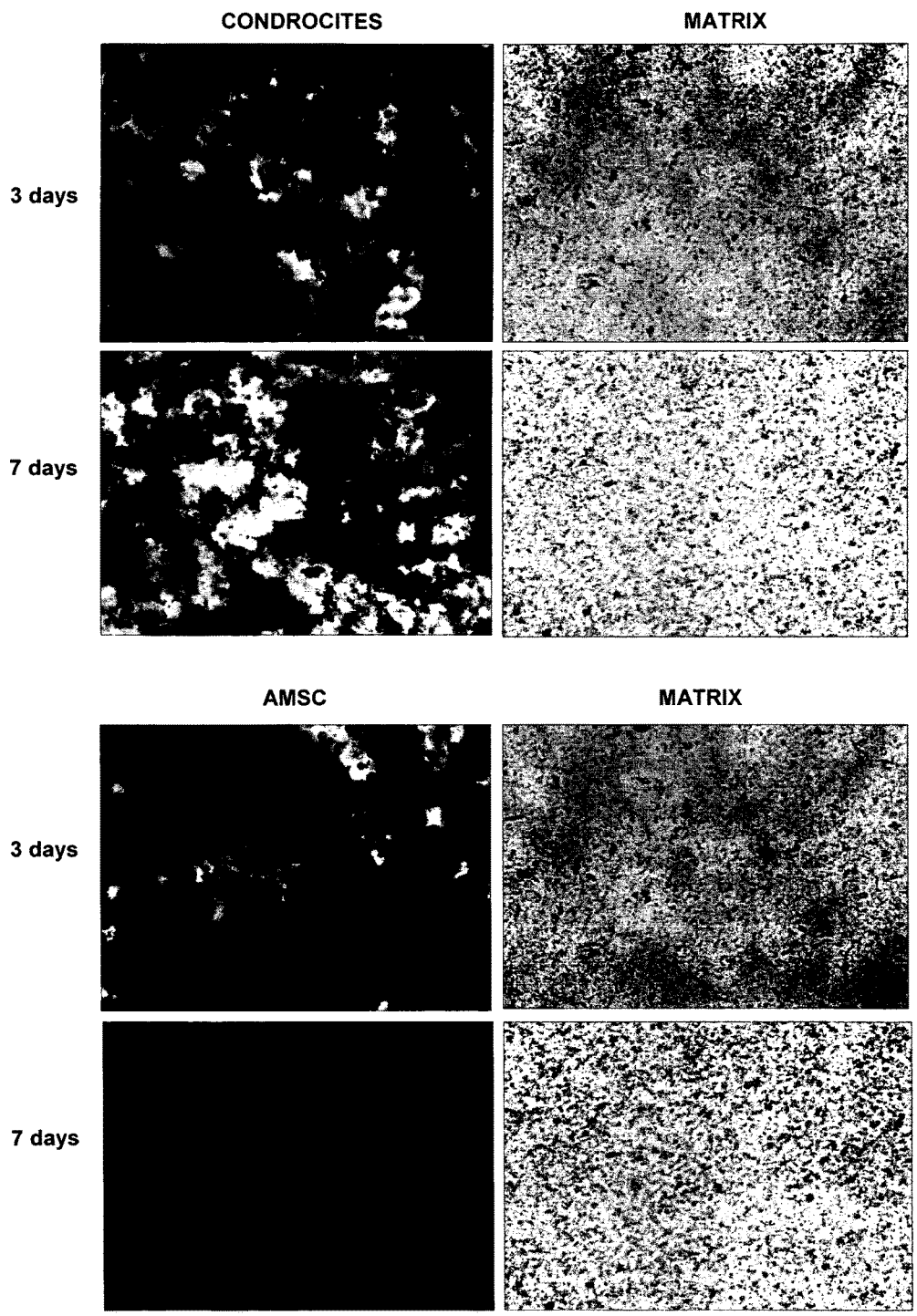
FIG. 6: Inverted light microscopy image that shows viability of articular cartilage cells (chondrocytes) and MSCs stained with MTT in coculture in the biomaterial of the present invention. Staining is at both 3 and 7 days. The black-stained cells are viable and metabolically active.

FIG. 6. Inverted light microscopy image that shows viability of articular cartilage cells (chondrocytes) and MSCs stained with MTT in coculture in the biomaterial of the present invention. Staining is at both 3 and 7 days. The black-stained cells are viable and metabolically active. In summary, based on the results presented in FIG. 6, the biomaterial of the current invention maintains cell viability versus control in the tested cell assemblage.

Example 12. Proliferative Capacity of Cells Grown in the Present Invention Compared to Hyaluronanic Acid (HA)

Figure 7:
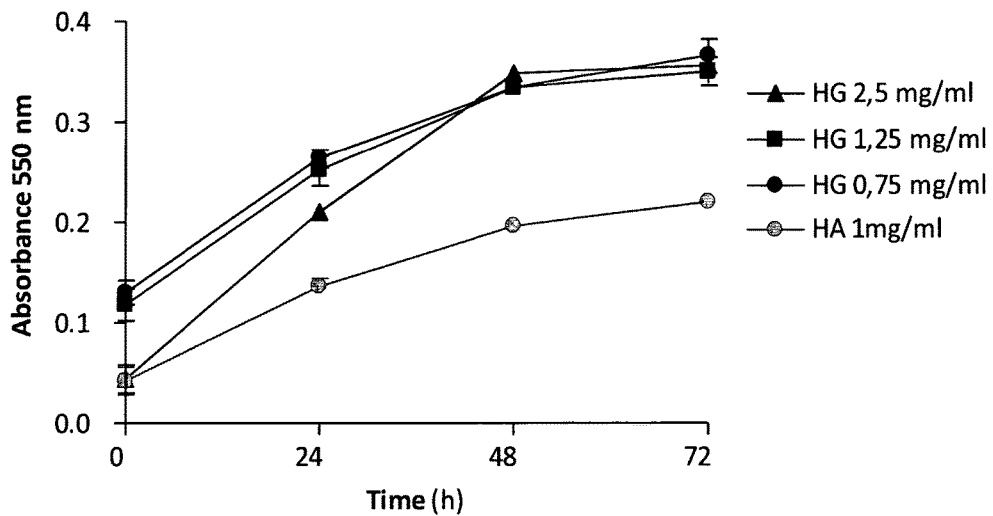
FIG. 7: A comparison of the proliferative capacity of human chondrocytes in the biomaterial of the present invention and in hyaluronic acid. The data in the graph shows a significant increase in proliferation capacity of chondrocytes maintained in the biomaterial of the present invention with respect to those cultured in hyaluronic acid.
Figure 8:
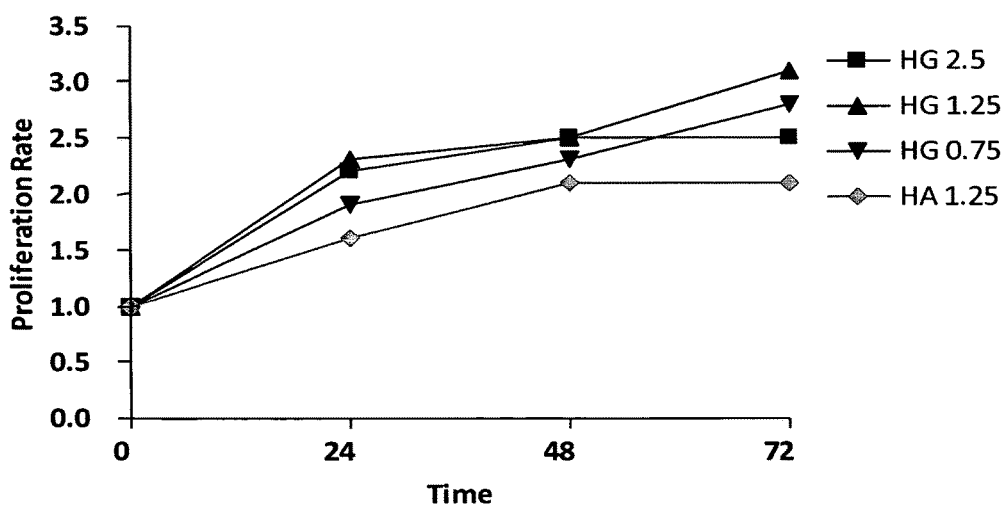
FIG. 8: Rate of proliferation of the fibroblasts L-929 in contact with the biomaterial of the present invention and hyaluronic acid. The graph shows a significant increase in the proliferation of cells arranged in the biomaterial of the present invention when compared to cells cultured in hyaluronic acid.

The proliferative capacity of the cells in the biomaterial of the present invention and HA was carried out utilizing MTT, according to the technique described in example 8. Tested cells included: human chondrocytes, fibroblast L-929, human fibroblasts, and human adipose tissue (AMSC) mesenchymal stem cells. Proliferation was observed at 24, 48 and 72 hours of culture. FIGS. 7 and 8 both illustrate the proliferation and survival of cultured cells is significantly higher in the biomaterial of the present invention when compared to HA at similar concentrations.

Example 13. Affinity and Capacity for Three-Dimensional Growth of Cells in the Biomaterial of the Present Invention Compared to Hyaluronan Acid (HA)

An aim in utilizing the biomaterial of the present invention is to enhance cellular recruitment to the area of injury from the surrounding tissue as well as act as a vehicle for the application of therapeutic cell populations to an injury. Thus, the importance of the biomaterial of the present invention in maintaining cell homeostasis is apparent.

To determine the capacity of the chondrocytes to form aggregates inside the biomaterial of the present invention, we cultured 750 k chondrocytes per well in 6 well plates with either 1.0 or 2.0 mg/mL of the biomaterial of the present invention. 72 hours after the start of the culture, the chondrocytes were observed to form clusters in the hydrogel at 2.0 mg/mL of concentration while there were no aggregations in the hydrogel at 1.0 mg/mL. 96 hours after the start of culturing, the chondrocytes in 2.0 mg/mL of biomaterial of the present invention were completely aggregated in clusters while those in the 1.0 mg/mL hydrogel commence to form clusters. In other words, aggregation and cluster formation readily occurs in the higher concentration of the material of the present invention when compared to control.

Figure 9:
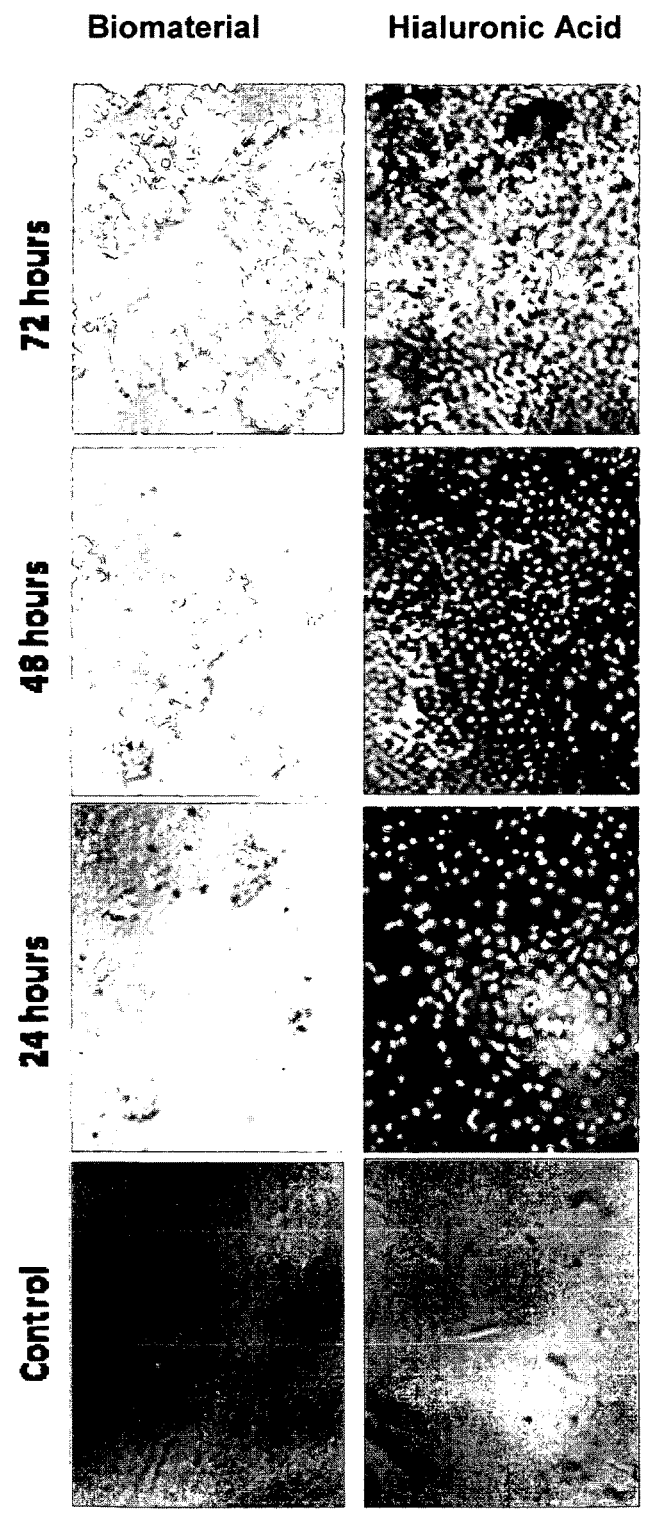
FIG. 9: Inverted fluorescence microscopy image of cells seeded on cell culture plastic, with the biomaterial of the present invention, and hyaluronic acid hydrogels placed in contact with the cell culture surface. In these images, cells in contact with the biomaterial of the present invention can be observed to detach from the cell culture surface and to form clusters within the biomaterial of the present invention.

Cells arranged in contact with the biomaterial of the present invention demonstrate a higher affinity for the biomaterial of the present invention over that of standard cell culture plastic surfaces. They detach from the cell culture plate and migrate into the biomaterial of the present invention where they form viable clusters. However, when using the same concentration of HA as a control, cells demonstrate a higher affinity for the cell culture plastic. At the same concentrations there are substantial differences in consistency between the biomaterial of the present invention and HA. HA is less viscous than the biomaterial of the present invention. FIG. 9 illustrates this migratory effect seen in the biomaterial of the current invention when compared to HA. Live/dead assay was used to delineate viable (green) cells from non-viable (red) cells. In conclusion, the cells utilized in this experiment have a greater affinity for the biomaterial of the present invention than cell culture plastic, a finding that is not repeated for HA and plastic.

Example 14. An Observation of the Functionality of Cells Cultured in the Present Invention Versus Cells Cultured in HA In this example the expression of markers associated with tissue regeneration was determined.

To determine the expression of different cartilage markers in MSC in the biomaterial of the present invention and control HA, the cells were cultured in T75 flasks with $7.5 \times 10^5$ cells per flask in two different concentrations of the hydrogel (0.1 and 0.5 mg/mL) and HA. After four days RNA was extracted from the samples by centrifugation of the cells and subsequent purification of the RNA with the Agilent total RNA isolation mini kit (Agilent technologies, USA). Following RNA extraction, cDNA was synthesized and RT-PCR was carried out according to standard protocols for the expression of Collagen type II and Versican.

FIG. 10 illustrates the results from gene expression analyses of the cartilage factors Collagen II and Versican from MSCs cultured in the biomaterial of the present invention versus an HA control. Type II collagen forms the majority of the articular cartilage matrix (90%) and is a marker of cellular differentiation towards the chondrocyte phenotype. The MSCs cultured in the biomaterial of the present invention commence the expression of type II collagen following 4 days of culture, a phenomenon not seen when they are cultured in HA. Versican is a minor component in the extracellular matrix of cartilage. It is considered a marker of dedifferentiation or loss of the chondrocyte phenotype in previously chondrocyte-like cells. As chondrocyte directed cells mature, they express less Versican and concomitantly increase their expression of agrecan, chondroitin sulfate, and collagen II. MSCs in the biomaterial of the present invention compared to the control population of cells in concentration-matched HA demonstrate a reduction in expression of the gene Versican with and increased expression of Collagen II. Therefore, the biomaterial of the present invention indicates an induction of differentiation of the chondrocyte phenotype or the capacity for synthesis of molecules related to articular cartilage regeneration.

Example 15. Rheometric Characterization of the Biomaterial of the Present Invention Derived from Human and Porcine Sources Mechanical characterizations of biomaterials are routinely conducted in order to provide both relevant and comparative information about tissue engineering scaffolds. With hydrogels, mechanical studies can provide important information about the suitability of a hydrogel for injection using various techniques, or the degree of completion of a chemical process such as crosslinking.

In this example, GAG scaffolds isolated from WJ as previously described were aliquoted into three percent solutions (1%, 5%, 10%) in respective 2 ml volumes in order to evaluate the effect of concentration on rheological parameters. A TA Instruments model AR2000ex rheometer was employed in the experiment. First, for each sample, a strain sweep was conducted in order to confirm that each sample was tested within its linear viscoelastic range (data not shown) in later studies involving storage and loss modulus, as well as viscosity.

Following determination of linear viscoelastic range, loss modulus, storage modulus, and viscosity were determined for each sample with constant frequency over a physiologically relevant temperature sweep varying from 20° C. to 50° C. Data were plotted and are presented in FIGS. 11-13.

In FIG. 11, Human values of 10% concentration were higher than porcine values at 10% concentration. Human values at 5% exceeded those of porcine at 5%. The results at lower concentrations (1% for both, and 5% for porcine) had a lower signal to noise ratio because of interial qualities of the viscometer cone. Quantitatively and qualitatively, human samples compared on a gram basis with porcine samples exhibited larger moduli. Moreover, a slight decrease in moduli is seen over the tested temperature change—a finding consistent with viscoelastic temperature effects at changing temperature under constant oscillation frequency. In FIG. 12, results from human values exceeded those of porcine samples over respective concentrations. The results at lower concentrations (1% for both, and 5% for porcine) had a low signal to noise ratio because of interial qualities of the viscometer cone. As in the storage modulus results, an expected slight decrease in moduli with temperature is seen. Loss modulus values are higher than storage modulus values in all respective cases thus indicating the dominance of viscous effects over elastive effects. This is an expected finding given that the isolated GAGs are a non-crosslinked hydrogel with inherent flow behavior. Loss modulus results for three different concentrations of the biomaterial of the present invention derived from porcine and human sources. In FIG. 13, results from human values exceeded those of porcine samples over respective concentrations. The results at lower concentrations (1% for both, and 5% for porcine) had a low signal to noise ratio because of the interial qualities of the viscometer cone. A wide range of viscosities is possible through varying the concentration of the samples although on a per gram basis, human hydrogel is consistently more viscous. A 10% solution of the human biomaterial of the present invention in this example possesses an average viscosity similar to that of castor oil.

In conclusion, a wide variety of viscosities and moduli are available by merely adjusting the concentration of the extracted GAGs.

Example 16. Cellular Recruitment from Surrounding Tissues (Chemotaxis)

The objective of this test was to determine the chemotactic capacity of the biomaterial of the present invention for the cells from a tissue. For this, we used samples of human cartilage from two different human patients. As the concentration of 2 mg/mL has proven adequate in tests of viability and proliferation for MSCs and chondrocytes, this concentration was utilized in the current example. Non-adherent plates were utilized to avoid the presence of a pro-attachment substrate) Experimental setup was as follows:

Negative control: Fragment in DMEM

Hyaluronic acid: Fragment in HA at 2 mg/mL

Figure 14:
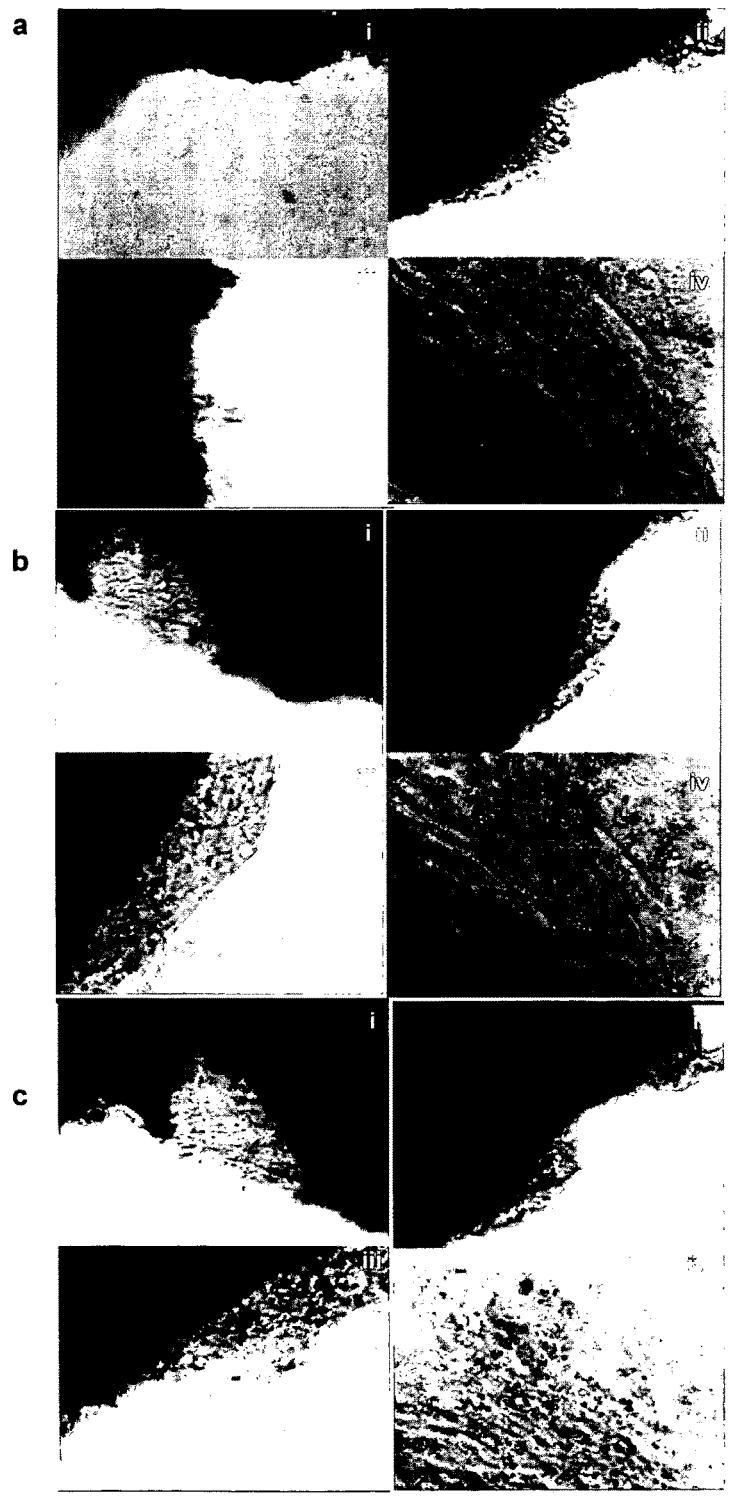
FIG. 14: Images of optical microscopy showing the cellular recruitment from surrounding tissues (chemotaxis) in days 1 (a), 3 (b) and 4 (c); wherein (i) corresponds to the positive control, (ii) corresponds to the hialuronic acid experimental set up, (iii) corresponds to the negative control and (iv) corresponds to the biomaterial of the invention experimental set up.
Figure 15:
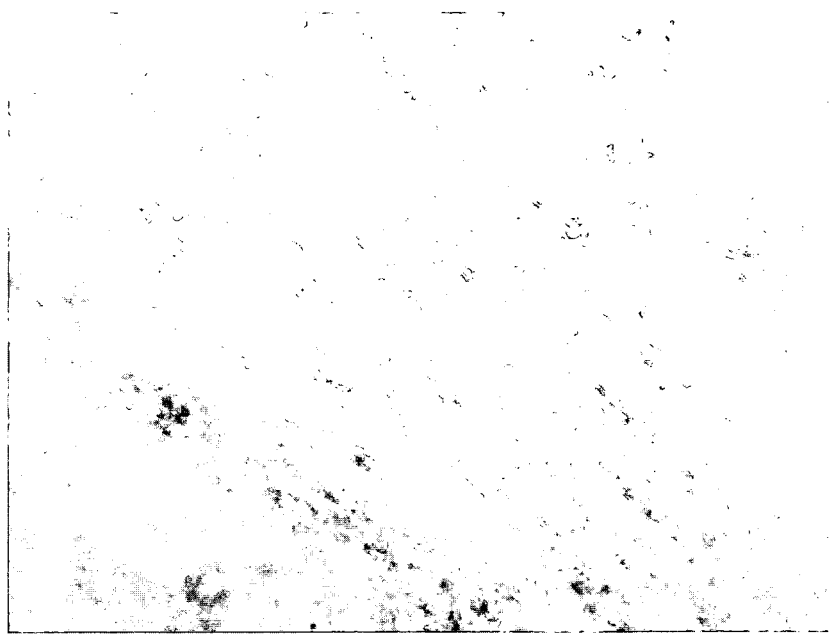
FIG. 15: Images of optical microscopy showing after performing a Live/Dead assay to determine whether or not the cells migrating to the surface of the cartilage fragments were viable. The image shows the vast majority of cells emerging from the cartilage fragments are viable.
Figure 16:
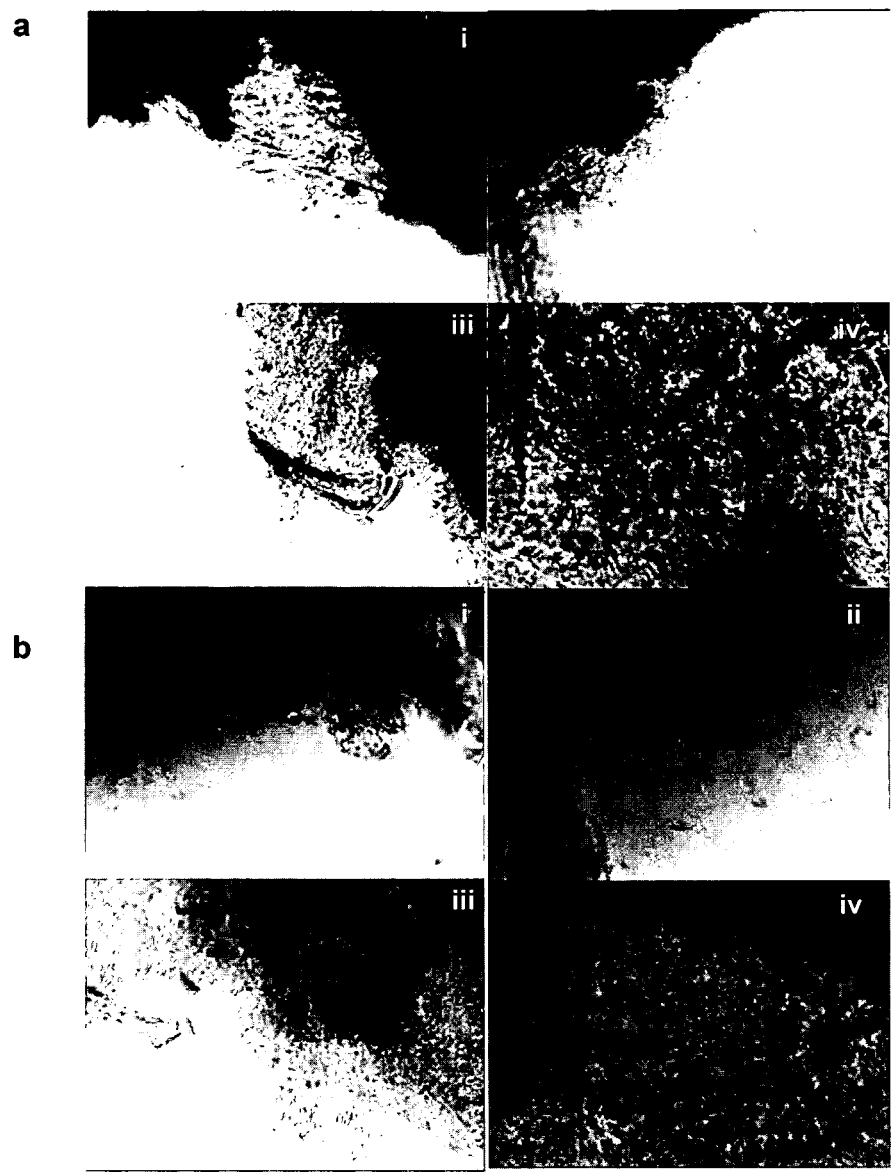
FIG. 16: Images of optical microscopy showing the cellular recruitment from surrounding tissues (chemotaxis) in days 5 (a) and 6 (b); wherein (i) corresponds to the positive control, (ii) corresponds to the hialuronic acid experimental set up, (iii) corresponds to the negative control and (iv) corresponds to the biomaterial of the invention experimental set up.

Material of interest: Fragment in the biomaterial of the present invention to 2 mg/mL Moreover, as a positive control, a sticky plaque was utilized. The tissue was cultured in DMEM supplemented with 10% fetal bovine serum. Images were collected daily and are presented in FIG. 14. Results show no cells in any of the controls or in the HA-exposed fragment. However, in the fragment that was in the biomaterial of the present invention, it was observed that a large number of cells have migrated to the outside surface of the cartilage from the earliest time point. Live/Dead assay was utilized to determine whether or not the cells migrating to the surface of the cartilage fragments were viable. The results are shown in FIG. 15 and indicate that the vast majority of cells emerging from the cartilage fragments are viable. However, no cells were observed to migrate from the surface of the cartilage fragments to the surrounding biomaterial of the present invention.

Based on this set of results we can conclude:

1. The biomaterial of the present invention possesses the ability to recruit cartilage cells from native tissue.
2. The cartilage cells that are recruited by the biomaterial of the present invention are viable.

As various possible embodiments might be made of the above invention, and as various changes might be made in the embodiments set forth above, it is to be understood that all matters herein described are to be interpreted as illustrative and not in a limiting sense.

REFERENCES

Collins M. N, Birkinshaw C. 2008. "Physical properties of crosslinked hyaluronic acid hydrogels". Journal of Material Science. Materials in Medicine, 19: 3335-3343.

Coburn I. A, Pandit A. 2007. "Development of naturally-derived biomaterials and optimization of their biomechanical properties". Topics in Tissue Engineering, 3: 1-14.

Cui F. Z, Tian W. M, Hou S. P, Xu Q. Y, Lee I. S. 2006. "Hyaluronic acid hydrogel immobilized with RGD peptides for brain tissue engineering". Journal of Material Science. Materials in Medicine, 17: 1393-1401.

Danishefsky I, Bella Jr. A. 1996. "The sulfated mucopolysaccharides from human umbilical cord", J. of Biological Chemistry, 241: 143-146.

Dawson J. I, Oreffo R. 2008. "Bringing the regeneration gap: stem cells, biomaterials, and clinical translation in bone tissue engineering". Archives of Biochemistry and Biophysics, 473: 124-131.

Elisseeff J, Ruffner M, Kim T. G, Williams C. 2005. "Cellular photoencapsulation in hydrogels". Culture of Cells for Tissue Engineering, Chapter 9.

Goa K. L, Benfield P. 1994. "Hyaluronic acid. A review of its pharmacology and use as a surgical aid in ophthalmology, and its therapeutic potential in joint disease and wound healing." Drugs, 47: 536-566.

Gogiel T, Galewska Z, Jaworski S. 2005. "Pre-eclampsia-associated alterations in Wharton's jelly proteoglycans". Acta Biochim Pol, 52: 501-507.

Hadidian Z, Pirie N. W. 1948. "The preparation and some properties of hyaluronic acid from human umbilical cord". The Biochemical Journal, 42: 260-265.

Hiles M, Hodde J. 2006. "Tissue engineering a clinically useful extracellular matrix biomaterial". Int Urogynecol Journal, 17: 39-43.

Ishihara M, Obara K, Ishizuka T, Fujita M, Sato M, Masuoka K, Saito Y, Yura H, Matsui T, Hattori H, Kikuchi M, Kurita A. 2002. "Controlled release of fibroblasts growth factors and heparin from photocrosslinked chitosan hydrogels and subsequent effect on in vivo vascularization". Journal of Biomedical Materials Research, 78: 364-371.

Jeanloz R. W, Forchielli E. 1950. "Studies on hyaluronic acid and related substances I. Preparation of hyaluronic acid and derivatives from human umbilical cord". Journal of Biological Chemistry, 186: 495-511.

Kanematsu A, Yamamoto S, Ozeki M, Noguchi T, Kanatani I, Ogawa O, Tabata Y. 2003. "Collagenous matrices as release carriers of exogenous growth factors". Biomaterials, 25: 4513-4520.

Laurent T. C, Fraser J. R. E. 1992. "Hyaluronan". The FASEB Journal, 6: 2397-2404

Longaker M, Chiu E. S, Harrison M. R, Crombleholme, Langer J. C, Duncan B. W, Adzick N. S, Verrier E. D, Stern R. 1989. "Studies in fetal wound healing" Annals of Surgery, 210: 667-672.

Mahoney D. J, Aplin R. T, Calabro A, Hascall V. C, Day A. J. 2001. "Novel methods for the preparation and characterization of hyaluronan oligosaccharides of defined length". Glycobiology, 11: 1025-1033.

Malkowski A, Sobolewski K, Jaworski S, Bankowski E. 2007. "FGF binding by extracellular matrix components of Wharton's jelly". Acta Biochim Pol, 54: 357-363.

Moore R. D, Schoenberg M. D. 1957. "Studies on connective tissue. T. The polysaccharides of the human umbilical cord". A. M. A. Archives of pathology, 64: 39-45.

Pieper J. S, Oosterhof A, Dijkstra P. J, Veerkamp J. H, van Kuppevelt T. H. 1999. "Preparation and characterization of porous crosslinked collagenous matrices containing bioavailable chondroitin sulphate", Biomaterials, 20: 847-858.

Rabenstein D. L. 2002. "Heparin and heparin sulfate: structure and function". Natural products reports, 19: 312-331.

Rogers B. A, Murphy C. L, Cannon S. R, and Briggs T. W. R. 2006. "Topographical variation in glycosaminoglycan content in human articular cartilage". The Journal of Bone and Joint Surgery, 88: 1670-1674.

Sobolewski K, Malkowski A, Bankowski E, Jaworski S. 2005. "Wharton's jelly as a reservoir of peptide growth factors." Placenta, 26, 747-752.

Toole B. P. 2004. "Hyaluronan: from extracellular glue to pericellular cue". Nature Cancer Reviews, 4, 528-539.

Torres D. S, Freyman T. M, Yannas I. V, Spector M. 2000. "Tendon cell contraction of collagen-GAG matrices in vitro: effect of cross-linking. Biomaterials, 21, 607-619.

Trowbridge J. M, Gallo R. 2002. "Dermatan sulfate: new functions from an old glycosaminoglycan". Glycobiology, 12: 117-125.

Ueno N, Chakrabarti B, Garg H. G. Hyaluronic acid of human skin and post-burn scar: heterogeneity in primary structure and molecular weight". 1992. Biochem Int, 26: 787-796.

Wissink M. J. B, Beernink R, Pieper J. S, Poot A. A, Engbers G. H. M, Beugeling T, van Aken W. G, Feijen J. 2001. "Binding and release of basic fibroblast growth factor from heparinized collagen matrices", Biomaterials, 22: 2291-2299.

The invention claimed is:

1. A hydrogel biomaterial consisting of
   a) a crosslinked extract of Wharton's Jelly of non-human animal umbilical cord,
   b) optionally, an added crosslinking agent;
   c) optionally, cells not originally present in Wharton's Jelly; and
   d) optionally, a pharmaceutically acceptable carrier;
   wherein said extract consists of a mixture of glycosaminoglycans (GAGs) consisting of hyaluronic acid, keratan sulfate, chondroitin-6-sulfate, heparan sulfate, chondroitin-4-sulfate, dermatan sulfate and heparin and said extract is free of non-human animal umbilical cord membrane, blood vessels, and cells or cell remnants originally present in Wharton's Jelly.

2. The hydrogel biomaterial according to claim 1, wherein hyaluronic acid comprises 40-80% of the total GAGs.

3. The hydrogel biomaterial according to claim 1, wherein keratan sulfate comprises 2-25% of the total GAGs.

4. The hydrogel biomaterial according to claim 1, wherein chondroitin-6-sulfate comprises 3-10% of the total GAGs.

5. The hydrogel biomaterial according to claim 1, wherein heparan sulfate comprises 1-9% of the total GAGs.

6. The hydrogel biomaterial according to claim 1, wherein chondroitin-4-sulfate comprises 0.5-7% of the total GAGs.

7. The hydrogel biomaterial according to claim 1, wherein dermatan sulfate comprises 0.1-7% of the total GAGs.

8. The hydrogel biomaterial according to claim 1, wherein heparin comprises 0.05-3% of the total GAGs.

9. The hydrogel biomaterial according to claim 1, wherein said hydrogel biomaterial consists of 70% hyaluronic acid, 10% keratan sulfate, 7% chondroitin-6-sulfate, 5% heparan sulfate, 4% chondroitin-4-sulfate, 3% dermatan sulfate and 1% heparin.

10. The hydrogel biomaterial according to claim 1, wherein said hydrogel biomaterial has a viscosity of 10 cS-150,000 cS.

11. The hydrogel biomaterial according to claim 10, wherein said viscosity is between 10 and 15,000 cS.

12. The hydrogel biomaterial according to claim 11, wherein said viscosity is between 10 to 2,000 cS.

13. The hydrogel biomaterial according to claim 12, wherein said hydrogel biomaterial has a substantially porous structure with a pore diameter of 0.5-1000 µm.

14. The hydrogel biomaterial according to claim 13, wherein said pore diameter is between 0.5-500 µm.

15. The hydrogel biomaterial according to claim 1, wherein said cells not originally present in the Wharton's Jelly are selected from the group consisting of undifferentiated mesenchymal stem cells; mesenchymal stem cells differentiated into another cell strain; undifferentiated hematopoietic stem cells or hematopoietic stem cells differentiated into another cell strain; chondrocytes; chondroblasts; osteoblasts; osteocytes; keratinocytes; fibroblasts and/or myocytes; adipocytes; neurons; cells from the nervous system; cells from the white blood cell system; corneal cells; endothelial cells: and epithelial cells.

16. A composite consisting of the hydrogel biomaterial according to claim 1, and an added reinforcing material.

17. A process for obtaining the hydrogel biomaterial according to claim 1, comprising the following steps:
   a) Obtaining a non-human animal umbilical cord;
   b) Treating the umbilical cord with a saline solution and antibiotics;
   c) Eliminating all the blood from the surface of the cord;
   d) Fragmenting the cord into sections of 1-2 cm;
   e) Cleaning out all the blood retained inside;
   f) Eliminating the umbilical cord membrane and blood vessels;
   g) Separating the gelatinous substance comprising Wharton's jelly;
   h) Enzymatically digesting the gelatinous substance obtained;
   i) Precipitating and isolating a mixture of GAGs consisting of hyaluronic acid, keratan sulfate, chondroitin-6-sulfate, heparan sulfate, chondroitin-4-sulfate, dermatan sulfate and heparin from the gelatinous substance, wherein the mixture is free of non-human animal umbilical cord membrane, blood vessels and cells present originally in Wharton Jelly;
   j) Resuspending the solid precipitate of GAGs in water; and
   k) Cross-linking the mixture of GAGs.

18. The process for obtaining the hydrogel biomaterial according to claim 17, wherein the cross-linking is covalent crosslinking carried out by chemical reactions.

19. The process for obtaining the hydrogel biomaterial according to claim 17, wherein the cross-linking produces ionic cross-links.

* * * * *